(12) United States Patent
Gaskins et al.

(10) Patent No.: US 10,905,801 B2
(45) Date of Patent: Feb. 2, 2021

(54) DEVICE AND PROCESS FOR PRODUCING FIBER PRODUCTS AND FIBER PRODUCTS PRODUCED THEREBY

(71) Applicant: LifeNet Health, Virginia Beach, VA (US)

(72) Inventors: Barton D. Gaskins, Virginia Beach, VA (US); Dennis L. Phelps, Virginia Beach, VA (US); Daniel B. Osborne, Virginia Beach, VA (US); Louis E. Ford, Virginia Beach, VA (US); Lloyd Wolfinbarger, Jr., Virginia Beach, VA (US)

(73) Assignee: LifeNet Health, Virginia Beach, VA (US)

( * ) Notice: Subject to any disclaimer, the term of this patent is extended or adjusted under 35 U.S.C. 154(b) by 0 days.

(21) Appl. No.: 15/494,001

(22) Filed: Apr. 21, 2017

(65) Prior Publication Data
US 2017/0266348 A1    Sep. 21, 2017

Related U.S. Application Data

(60) Continuation of application No. 12/692,879, filed on Jan. 25, 2010, now abandoned, which is a division of
(Continued)

(51) Int. Cl.
*A61F 2/28* (2006.01)
*A61L 27/38* (2006.01)
(Continued)

(52) U.S. Cl.
CPC ...... *A61L 27/3821* (2013.01); *A61B 17/1635* (2013.01); *A61F 2/28* (2013.01);
(Continued)

(58) Field of Classification Search
CPC ............. A61F 2/28; A61F 2002/4645; A61F 2310/00359; A61F 2/2415; A61F 2/3094;
(Continued)

(56) References Cited

U.S. PATENT DOCUMENTS

| | | | |
|---|---|---|---|
| 2,991,814 | A | 7/1961 | Popeil |
| 3,856,219 | A | 12/1974 | Stayton et al. |

(Continued)

FOREIGN PATENT DOCUMENTS

| | | |
|---|---|---|
| KR | 20080081053 A | 9/2008 |
| WO | 2010050935 A1 | 5/2010 |

OTHER PUBLICATIONS

Goodman et al. (1996) Three-Dimensional Extracellular Matrix Biomaterials, Biomaterials, 17(21):2087-2095.
(Continued)

*Primary Examiner* — Ann Schillinger
(74) *Attorney, Agent, or Firm* — RatnerPrestia

(57) ABSTRACT

The present invention is directed to a fiber, preferably bone fiber, having a textured surface, which acts as an effective binding substrate for bone-forming cells and for the induction or promotion of new bone growth by bone-forming cells, which bind to the fiber. Methods of using the bone fibers to induce or promote new bone growth and bone material compositions comprising the bone fibers are also described. The invention further relates to a substrate cutter device and cutter, which are effective in producing substrate fibers, such as bone fibers.

20 Claims, 23 Drawing Sheets

Related U.S. Application Data application No. 10/606,208, filed on Jun. 26, 2003, now Pat. No. 7,744,597.

(60) Provisional application No. 60/391,323, filed on Jun. 26, 2002.

(51) Int. Cl.
*A61B 17/16* (2006.01)
*A61F 2/46* (2006.01)
*A61L 27/36* (2006.01)

(52) U.S. Cl.
CPC .......... *A61F 2/4644* (2013.01); *A61L 27/365* (2013.01); *A61L 27/3608* (2013.01); *A61L 27/3691* (2013.01); *A61F 2002/2817* (2013.01); *A61F 2002/4649* (2013.01); *A61L 2430/02* (2013.01)

(58) Field of Classification Search
CPC .. A61L 27/3608; A61L 2430/02; A61L 27/54; A61L 2300/414; A61L 27/365; A61L 27/3834; A61L 27/3604; A61L 27/3847; A61L 27/3821; A61L 2430/38
See application file for complete search history.

(56) References Cited

U.S. PATENT DOCUMENTS

| | | | |
|---|---|---|---|
| 4,212,431 A | 7/1980 | Doyel | |
| 4,271,740 A | 6/1981 | Yamazaki et al. | |
| 4,485,096 A | 11/1984 | Bell | |
| 4,485,097 A | 11/1984 | Bell | |
| 4,553,272 A | 11/1985 | Mears | |
| 4,637,931 A | 1/1987 | Schmitz | |
| 4,721,104 A | 1/1988 | Kaufman et al. | |
| 4,963,489 A | 10/1990 | Naughton et al. | |
| 5,073,373 A | 12/1991 | O'Leary et al. | |
| 5,098,636 A | 3/1992 | Balk | |
| 5,106,365 A | 4/1992 | Hernandez | |
| 5,209,745 A | 5/1993 | Irr et al. | |
| 5,263,985 A | 11/1993 | Bao et al. | |
| 5,275,954 A | 1/1994 | Wolfinbarger et al. | |
| 5,284,655 A | 2/1994 | Bogdansky et al. | |
| 5,290,558 A | 3/1994 | O'Leary et al. | |
| 5,298,254 A | 3/1994 | Prewett et al. | |
| 5,306,305 A | 4/1994 | Lee | |
| 5,314,476 A | 5/1994 | Prewett et al. | |
| 5,366,507 A | 11/1994 | Sottosanti | |
| 5,382,249 A | 1/1995 | Fletcher | |
| 5,405,390 A | 4/1995 | O'Leary et al. | |
| 5,484,601 A | 1/1996 | O'Leary et al. | |
| 5,506,117 A | 4/1996 | Andrews et al. | |
| 5,507,813 A | 4/1996 | Dowd et al. | |
| 5,510,396 A | 4/1996 | Prewett et al. | |
| 5,531,791 A | 7/1996 | Wolfinbarger, Jr. | |
| 5,607,269 A | 3/1997 | Dowd et al. | |
| 5,622,857 A | 4/1997 | Goffe | |
| 5,634,879 A | 6/1997 | Mueller-Glauser et al. | |
| 5,674,292 A | 10/1997 | Tucker et al. | |
| 5,745,999 A | 5/1998 | Zirkiev | |
| 5,752,425 A | 5/1998 | Asakura et al. | |
| 5,820,581 A | 10/1998 | Wolfinbarer, Jr. | |
| 5,824,084 A * | 10/1998 | Muschler ............... A61F 2/4644 128/898 |
| 5,843,182 A | 12/1998 | Goldstein | |
| 5,855,617 A | 1/1999 | Orton | |
| 5,882,929 A | 3/1999 | Fofonoff et al. | |
| 5,899,936 A | 5/1999 | Goldstein | |
| 5,918,821 A | 7/1999 | Grooms et al. | |
| 5,948,426 A | 9/1999 | Jeffries | |
| 5,948,428 A | 9/1999 | Lee et al. | |
| 5,972,703 A * | 10/1999 | Long ............... C12N 5/0654 424/139.1 |
| 6,012,660 A | 1/2000 | Colman | |
| 6,013,856 A | 1/2000 | Tucker et al. | |
| 6,028,242 A | 2/2000 | Tucker et al. | |
| 6,049,026 A | 4/2000 | Muschler | |
| 6,180,606 B1 | 1/2001 | Chen et al. | |
| 6,189,537 B1 | 2/2001 | Wolfinbarger, Jr. | |
| 6,214,049 B1 | 4/2001 | Gayer et al. | |
| 6,305,379 B1 | 10/2001 | Wolfinbarger, Jr. | |
| 6,372,257 B1 | 4/2002 | Marchosky | |
| 6,375,663 B1 | 4/2002 | Ebner et al. | |
| 6,402,070 B1 | 6/2002 | Ishida et al. | |
| 6,416,995 B1 | 7/2002 | Wolfinbarger, Jr. | |
| 6,458,375 B1 * | 10/2002 | Gertzman ............... A61F 2/28 424/422 |
| 6,461,630 B1 | 10/2002 | Tucker et al. | |
| 6,504,079 B2 | 1/2003 | Tucker et al. | |
| 6,534,095 B1 | 3/2003 | Moore-Smith et al. | |
| 6,541,024 B1 | 4/2003 | Kadiyala et al. | |
| 6,576,249 B1 | 6/2003 | Gendler et al. | |
| 6,607,910 B1 | 8/2003 | Dimitrijevich et al. | |
| 6,648,133 B1 | 11/2003 | Blaschke et al. | |
| 6,679,918 B1 | 1/2004 | Benedict et al. | |
| 6,755,365 B1 | 6/2004 | Meredith | |
| 6,933,326 B1 | 8/2005 | Griffey et al. | |
| 7,494,811 B2 * | 2/2009 | Wolfinbarger, Jr. ... C12M 21/08 435/373 |
| 7,498,040 B2 | 3/2009 | Masinaei | |
| 7,498,041 B2 | 3/2009 | Masinaei | |
| 7,744,597 B2 | 6/2010 | Gaskins et al. | |
| 7,824,711 B2 | 11/2010 | Kizer et al. | |
| 7,977,094 B2 | 7/2011 | Masinaei | |
| 8,002,813 B2 | 8/2011 | Scarborough et al. | |
| 8,309,106 B2 | 11/2012 | Masinaei | |
| 8,883,210 B1 | 11/2014 | Truncale et al. | |
| 9,005,646 B2 | 4/2015 | Masinaei et al. | |
| 9,034,644 B2 | 5/2015 | Masinaei | |
| 9,352,003 B1 | 5/2016 | Semler et al. | |
| 9,962,467 B2 | 5/2018 | Masinaei et al. | |
| 2001/0033857 A1 * | 10/2001 | Vyakarnam ............... A61F 2/28 424/443 |
| 2002/0035401 A1 * | 3/2002 | Boyce ...................... A61F 2/28 623/23.51 |
| 2002/0037586 A1 | 3/2002 | Takagi et al. | |
| 2002/0048563 A1 * | 4/2002 | Baetge .................... A61L 15/40 424/93.7 |
| 2002/0070299 A1 | 6/2002 | Lenox | |
| 2002/0106625 A1 | 8/2002 | Hung et al. | |
| 2002/0108478 A1 | 8/2002 | Klimack et al. | |
| 2002/0120347 A1 | 8/2002 | Boyer, II et al. | |
| 2002/0161449 A1 | 10/2002 | Muschler | |
| 2003/0012821 A1 | 1/2003 | O'Leary et al. | |
| 2003/0014124 A1 | 1/2003 | Wolfinbarger, Jr. et al. | |
| 2003/0100108 A1 | 5/2003 | Altman et al. | |
| 2003/0143207 A1 * | 7/2003 | Livesey .................. A61K 35/32 424/93.7 |
| 2003/0144743 A1 | 7/2003 | Edwards et al. | |
| 2003/0185803 A1 * | 10/2003 | Kadiyala ............. A61L 27/3608 424/93.7 |
| 2004/0059364 A1 | 3/2004 | Gaskins et al. | |
| 2004/0062816 A1 | 4/2004 | Atkinson et al. | |
| 2004/0071668 A1 | 4/2004 | Bays et al. | |
| 2005/0059952 A1 | 3/2005 | Giuliano et al. | |
| 2005/0226904 A1 | 10/2005 | Choi et al. | |
| 2006/0024656 A1 | 2/2006 | Morris et al. | |
| 2007/0105222 A1 | 5/2007 | Wolfinbarger, Jr. et al. | |
| 2007/0162132 A1 | 7/2007 | Messerli | |
| 2007/0191963 A1 | 8/2007 | Winterbottom et al. | |
| 2008/0234654 A1 | 9/2008 | McCarthy et al. | |
| 2008/0254471 A1 | 10/2008 | Bordano | |
| 2008/0262633 A1 | 10/2008 | Williams et al. | |
| 2009/0030396 A1 | 1/2009 | Ferris | |
| 2011/0160857 A1 | 6/2011 | Bracone et al. | |

OTHER PUBLICATIONS

Holland et al. (1996) Culture of Human Vascular Endothelial Cells on an RGD-Containing Synthetic Peptide Attached to a Starch-Coated Polystyrene Surface: Comparison with Fibronectin-Coated Tissue Grade Polystyrene, Biomaterials, 17(22):2147-2156.

(56) References Cited

OTHER PUBLICATIONS

Jain et al. (2003) Fibroblast Attachment to Smooth and Microtextured PET and Thin cp-Ti Films, Wiley InterScience (www.interscience.com), Dec. 17, 2003, pp. 296-304, Wiley Periodicals, Inc., USA.

Matsuzaka et al. (2003) Effects of Multigrooved Surfaces on Osteoblast-Like Cells in vitro: Scanning Electron Microscopic Observation and mRNA Expression of Osteopontin and Osteocalcin, Wiley InterScience (www.interscience.com) Dec. 9, 2003, pp. 227-234, Wiley Periodicals, Inc., USA.

Schmidt et al. (1992) Macrophage Response in Microtextured Silicon, Biomaterials, 13(15):1059-1069.

Non Final Office Action for U.S. Appl. No. 14/689,221, dated Jul. 15, 2016, 7 pages.

Rabie et al., J Dent Res., 75(4):1045-51 (1996).

Office Action for U.S. Appl. No. 12/692,879 dated Jun. 9, 2016 from U.S. Patent and Trademark Office.

Final Office Action for U.S. Appl. No. 12/692,879 dated Mar. 13, 2017 from U.S. Patent and Trademark Office.

Non Final Office Action for Application No. 15/904,670, dated Oct. 4, 2018, 25 pages.

Indian Examination Report for Indian Application No. 3084/KOLNP/2015, dated May 6, 2019 with translation, 7 pages.

Final Office Action for U.S. Appl. No. 14/769,694, dated Jan. 29, 2020, 18 pages.

Canadian Office Action for Canadian Application No. 2,902,155, dated Mar. 6, 2020, 4 pages.

Non Final Office Action for U.S. Appl. No. 16/179,173, dated Oct. 2, 2019, 32 pages.

Korean Office Action for Korean Application No. 10-2015-7026210, dated Mar. 4, 2020 with English translation, 10 pages.

Non Final Office Action for U.S. Appl. No. 14/769,694, dated Sep. 15, 2020, 11 pages.

European Communication Pursuant to Article 94(3) for European Application No. 14754747.5, dated Oct. 7, 2020, 4 pages.

\* cited by examiner

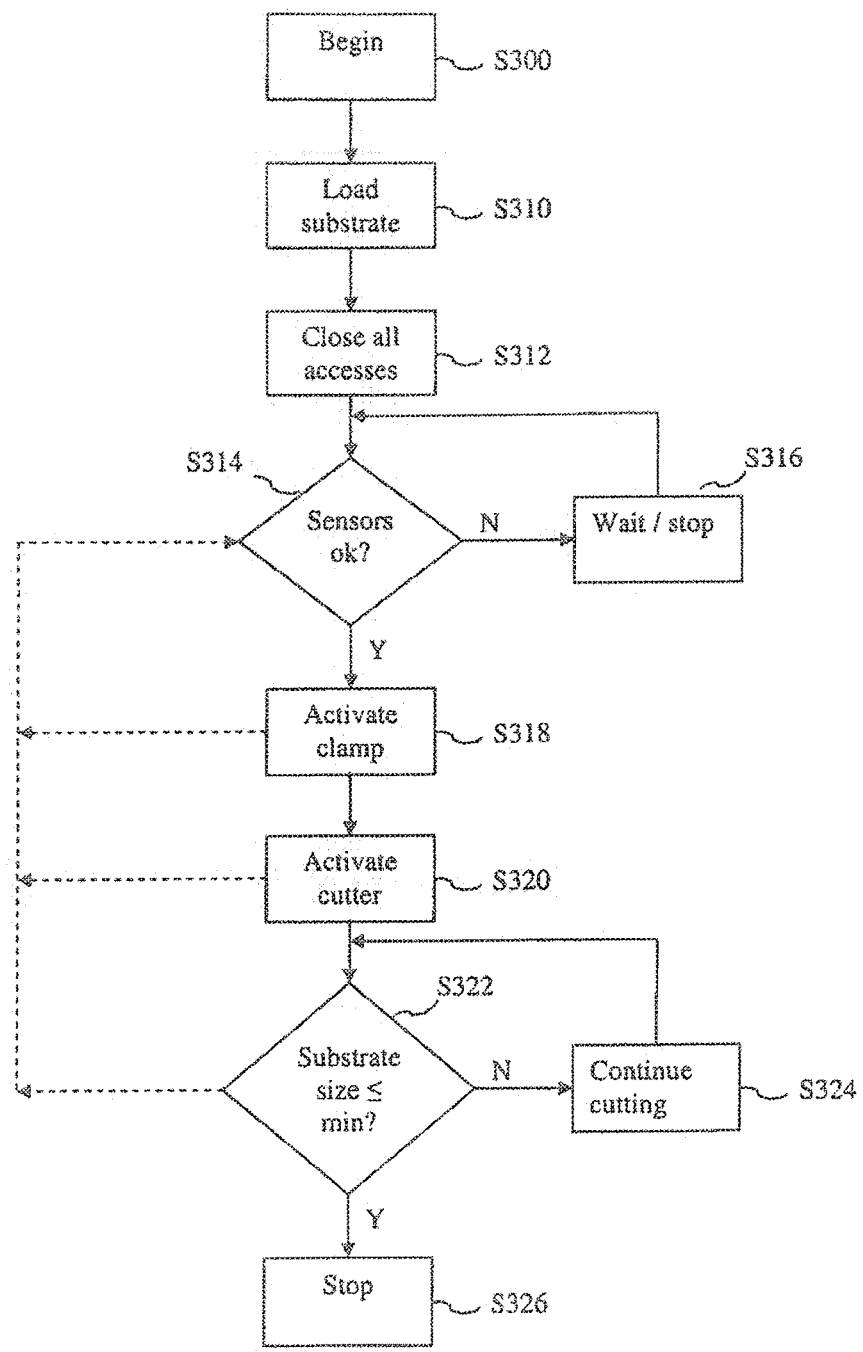

DEVICE AND PROCESS FOR PRODUCING FIBER PRODUCTS AND FIBER PRODUCTS PRODUCED THEREBY

CROSS-REFERENCE TO RELATED APPLICATIONS

This application is a Continuation of application of U.S. patent application Ser. No. 12/692,879, filed on Jan. 25, 2010; which is a Divisional application of U.S. patent application Ser. No. 10/606,208, filed on Jun. 26, 2003, now U.S. Pat. No. 7,744,597; which claims priority to and the benefit of U.S. Provisional Patent Application Ser. No. 60/391,323, filed Jun. 26, 2002, which are all hereby incorporated herein by reference in their entireties.

FIELD OF THE INVENTION

This invention relates to a cutting device for cutting a substrate, processes for the production of substrate fibers, and the substrate fibers produced. Suitable substrates include but are not limited to bone tissue, including allogenic and xenogenic cortical bone. The fibers are cut from a substrate using the device, such that an individual fiber produced has a length that is typically greater than 10 to 200 times its width and thickness. The invention further relates to compositions including bone fibers and other agents, including, for example, bioactive agents, including stem cells, which bind to the bone fibers and are induced to form new bone.

BACKGROUND OF THE INVENTION

Ground demineralized cortical and cancellous bone have been widely used in the induction of new bone formation for the treatment of a variety of clinical pathologies. Typically, the bone materials are obtained from human or animal sources, ground and demineralized. Such bone has been demonstrated over the past two decades to induce new bone formation when implanted in animal models, to stimulate elevated levels of the enzyme alkaline phosphatase, and to contain extractable amounts of bioactive molecules, such as bone morphogenetic proteins (BMPs).

The ground demineralized bone matrix (DBM) has also been called demineralized bone (DMB), and demineralized freeze-dried bone allograft (DFDBA). DFDBA materials are provided for clinical use in a freeze-dried state. DBM (or DMB) can be provided for clinical use in either a freeze-dried state or as a hydrated state—usually in some form of an aqueous carrier, for example, glycerol in GRAFTON™ (GRAFTON™ is a registered trademark of Osteotech, Inc., Shrewsbury, N.J.), pluronic polymer in DYNAGRAFT™ (DYNAGRAFT™ is a registered trademark of GenSci Regeneration Technologies, Inc., Irvine, Calif.) and collagen in OPTIFORM™ (OPTIFORM™ is a registered trademark of Regeneration Technologies, Inc., Alachua, Fla.). These various commercially available demineralized bone products primarily contain demineralized cortical ground bone distributed for clinical applications. The use of carriers with demineralized bone particles are more acceptable to clinicians because such particles acquire a static charge in the dry state making them difficult to dispense into containers and following rehydration, the clinician typically has difficulties in getting the bone particles to remain at the implant site and in a compacted state wherein they are presumed to be most osteoinductive. DBM is considered to be osteoinductive if it induces the formation of new bone, for example, at the site of clinical application. By adding carriers to the DBM, the biomaterials become easier to aliquot into containers and tend to remain tightly aggregated at the implant site making them easier to handle.

The osteoinductive nature of DBM arises from the interaction between bone-forming cells and the DBM. Such interaction takes place at both a molecular and physical level. At the molecular level, attachment of the bone-forming cells to the DBM involves the presence of "receptors" on the surface of the plasma membrane of mammalian cells that bind to "ligands" present on the surface of the biomaterial. An example of this type of attachment or binding is illustrated in the role of RGD-containing amino acid sequences in the attachment of mammalian cells to a wide variety of molecules present within matrices of tissues. The RGD amino acid sequence refers to the amino acids arginine (R), glycine (G), and aspartic acid (D). Holland, et al. (Biomaterials. 1996. 17(22):2147-56) described the research on a synthetic peptide, gly-arg-gly-asp-ser-pro-lys (GRGDSPK) (which includes the cell-adhesive region of fibronectin, and arg-gly-asp (RGD) peptide sequence covalently bound to a dialdehyde starch (DAS) coating on a polymer surface. The authors concluded that the GRGD-SPK/DAS-coated surface could be substituted for an adhesive-protein coated surface in the culture of anchorage-dependent cells.

On the other hand, binding at the physical level in the context of surface patterning has been described, for example, in Goodman, et al. (Biomaterials. 1996. 17(21): 2087-95). Goodman et al. described clinical and experimental investigations on manufactured surface topographies that have significant effects on cell adhesion and tissue integration stating that micro- and nano-scale mechanical stresses generated by cell-matrix adhesion have significant effects on cellular phenotypic behavior. Details of surface patterning effects on cell attachment and proliferation were described by Schmidt and Recum (Biomaterials. 1992. 13(15):1059-69) measuring macrophage responses to microtextured silicone. Schmidt and Recum measured the effects of seven different silicone surface textures on macrophage spreading and metabolic activity in vitro. Variables of the textured arrays important to cell spreading and metabolic activity included size, spacing between, depth, density, and orientation of the individual surface events and the roughness of the surfaces. It was found that pattern dimensions of about 5 microns textures were associated with small cells, whereas a smooth (untextured) surface was associated with large cells. The authors put forth a hypothesis that included a possible mechanism of how a micrometer-sized surface texture could modify cell function.

There are thus several issues pertinent to the ability of implanted bone compositions to induce the formation of bone. These issues include providing an environment suitable for the infiltration of cells, a confined environment that restricts the diffusion of synthesized matrix-forming molecules (for example, collagens, proteoglycans, and hyaluronins), promotes cell attachment to DMBs, and includes the presence of bioactive molecules (for example BMPs). Additionally, the method for making bone fibers for these bone implanted compositions in an efficient and consistent manner is addressed by the present invention.

SUMMARY OF THE INVENTION

The present invention is directed to a fiber, preferably bone fiber, having a textured surface, which acts as an effective binding substrate for bone-forming cells and for the induction or promotion of new bone growth by bone-forming cells, which bind to the fiber. The bone fiber of the present invention may be demineralized or mineralized, or may be used in a composition comprising a combination of demineralized and mineralized bone fibers and bone particles. The bone fibers of the invention may be made from any type of bone, such as allogenic or xenogenic bone. Preferably, the bone fiber is made from cortical bone or cancellous bone, more preferably cortical bone. The bone fiber may be of any length. Preferably, the bone fiber has an average length of from about 1 mm to about 100 mm, an average width of from about 0.5 mm to about 2.5 mm, and an average thickness of from about 0.2 mm to about 1.4 mm. The fiber may then be processed according to known processes. In a preferred embodiment, the bone is freeze-dried.

The present invention further is directed to bone material compositions comprising the bone fibers of the present invention. In a preferred embodiment of this aspect of the invention, the bone material composition comprises a bone fiber and bone-forming cells, wherein the bone fiber has a textured surface, which acts as an effective binding substrate for bone-forming cells, and wherein the composition induces or promotes new bone formation from the bone-forming cells bound to the bone fiber. Preferably, the bone-forming cells are selected from stem cells, connective tissue progenitor cells, fibroblast cells, periosteal cells, chondrocytes, osteocytes, pre-osteoblasts, and osteoblasts. Most preferably, the bone-forming cells are stem cells. The bone fibers used in the bone material composition may be any type of bone, including allogenic or xenogenic bone. Preferably, the bone fibers are comprised of cortical or cancellous bone, more preferably comprised of cortical bone. In addition, the composition may further comprise cancellous bone. The composition may further comprise both demineralized and non-demineralized bone fibers or bone particles. The bone material composition may further comprise an agent effective to initiate or promote the induction of bone growth.

Yet another aspect of the invention is a method for inducing or promoting bone growth. This method comprises providing a bone fiber according to the present invention, contacting the bone fiber to bone-forming cells, which adhere to the textured surface of the bone fiber, and wherein the binding induces or promotes new bone growth from the bone-forming cells. The method may further comprise contacting the bone fibers and bone-forming cells with an agent effective to initiate or promote the induction of the new bone growth. Suitable agents to induce or promote bone growth include bone morphogenic proteins, angiogenic factors, growth and differentiation factors, mitogenic factors, and osteogenic/chondrogenic factors. Preferably, the bone fiber used in the method is demineralized. Preferred bone-forming cells include stem cells, connective tissue progenitor cells, fibroblast cells, periosteal cells, chondrocytes, osteocytes, pre-osteoblasts, and osteoblasts. Preferably, the bone-forming cells are stem cells. Moreover, the bone-forming cells may be contacted to the bone fibers via a biological fluid. Preferably biological fluids include plasma, bone marrow, blood, or blood products.

According to another aspect of the present invention a cutter is provided for producing substrate fibers. The cutter preferably includes a leading edge designed to make initial contact with the substrate and a trailing edge. The trailing edge preferably is configured such that it is raised above the leading edge by a prescribed height. The cutter includes a cutting surface upon which a blade section is disposed. The blade section is used to cut the substrate. At least one substrate channel may be provided near the blade section in order to direct the substrate fibers away from the substrate.

According to one exemplary embodiment of the present invention, the blade section can include at least one row of teeth designed specifically for cutting the substrate. Furthermore, each tooth can be configured with at least one predetermined cutting angle to reduce stress and achieve desired substrate properties. For example, one specific implementation of the invention provides a preferred primary cutting angle ranging from 3-6. Preferably the primary cutting angle can be selected to be approximately 4. A secondary cutting angle can also be provided. The secondary cutting angle can vary between 10-18, but is preferably selected to be approximately 14.

According to another aspect of the invention, a substrate cutting device is provided. The substrate cutting device includes a base and a tower. The base further includes a cutter that can be moved along a predetermined cutting path. A substrate chute extends through the base in order to position the substrate in a location where it will be in contact with the cutter. The tower includes a lower surface, which contains a recess. The recess can be aligned with the substrate chute. A clamping mechanism is provided to keep the substrate in contact with the cutter during the cutting process. The substrate cutting device can further include a fiber receptacle to receive the substrate fibers after they have been cut.

According to one exemplary embodiment of the present invention, the base is mounted on a slide mechanism, which moves along the predetermined cutting path. An actuation unit, such as a pneumatic actuator, can be used to supply the force necessary for moving the slide mechanism. According to one specific implementation of the present invention, the first actuation generates a force ranging between 600 lbs-900 lbs, and preferably about 750 lbs. A second actuation unit can also be provided to control the clamping mechanism. The second actuation unit can be configured to generate a force ranging from 150 lbs-250 lbs, and preferably about 200 lbs. The present invention can also include a computer controller for controlling operation of the substrate cutting device, including the first and second actuation units. For example, the computer controller can be used to adjust the force applied by the first actuation unit and/or adjust the speed at which the slide mechanism is moving. The computer controller can also be used to adjust the force applied on the substrate during the cutting process.

According to another aspect of the present invention, a method for cutting a substrate comprises the steps: placing the substrate into a substrate cutting device; applying a predetermined force on the substrate; moving a substrate cutter along a grain direction of the substrate; cutting substrate fibers from the substrate; detecting when the substrate has reached a predetermined minimum thickness; and terminating the process if the substrate has reached the predetermined minimum thickness.

The present invention is further directed to the substrate fibers produced using the substrate cutting device of the present invention.

BRIEF DESCRIPTION OF THE DRAWINGS

(FIG. 2A), 37×. (FIG. 2B) and 13×. (FIG. 2C), which depict the parallel striations along the grain of the bone fibers and the serrated edges and grooves which are believed to foster attachment sites for bone-forming cells.

FIG. 19 is a flow chart showing the steps performed when cutting substrates.

DETAILED DESCRIPTION

Figure 1:
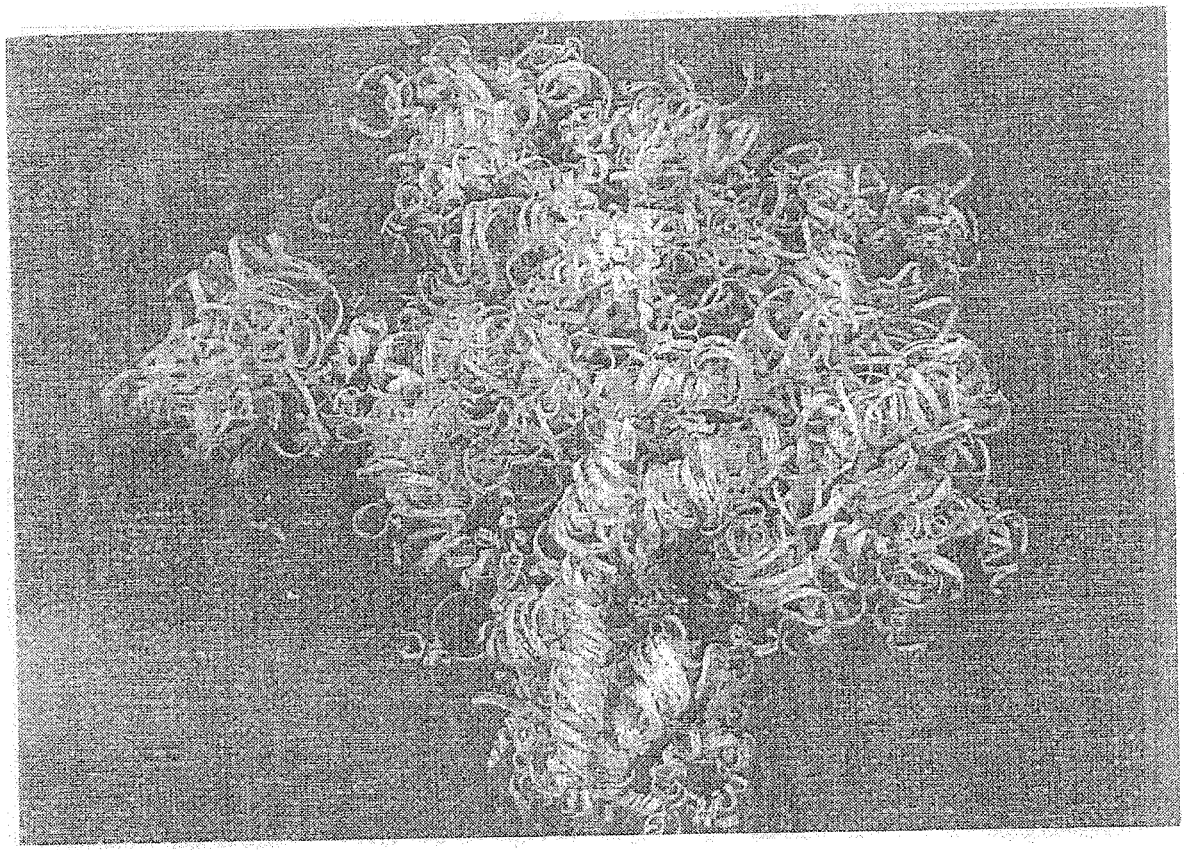
FIG. 1 illustrates fiber bone having a ribbon-like structure produced using an apparatus of the present invention.

The invention provides a bone fiber having surface properties that offer a suitable environment for the attachment of infiltrating cells, such that they can attach (normal mammalian cells are "attachment dependent" meaning they do not typically proliferate or maintain synthetic functions unless attached to a solid matrix) and synthesize bone matrix-forming molecules. Appropriate attachment surfaces can also contribute to the stimulation of cells to proliferate, differentiate, and to synthesize appropriate bone matrix-forming molecules.

The present invention is also directed to a method of making the bone fibers of the present invention involving the use of an apparatus suitable for cutting bone to produce fibers having the enhanced cell-binding surface to increase the bone-forming induction properties of demineralized bone material and to facilitate formation of a matrix suitable for perfusion, percolation, and infusion of viscous cell materials into the matrix.

Finally, the present invention is directed to an apparatus suitable for cutting a substrate. The apparatus includes a unique arrangement that allows the substrate to be cut into fibers having consistent properties for a particular application. A special cutter is used to cut the fibers along a grain direction of the substrate in order to produce substrate fibers. The apparatus includes various safety features, such as sensors to detect whether all access doors are shut prior to commencing operation. If a sensor is triggered during operation, the apparatus is immediately powered down in order to prevent an operator from being harmed. The present apparatus can also include a computer controller to control various operations.

I. Definitions

The terms used herein are given their plain, ordinary meaning as understood by those having ordinary skill in the art, unless otherwise defined herein.

The "bioactive agents" of the present invention refer to the agents capable of initiating and inducing the differentiation and/or proliferation of bone cells and/or the induction of bone cell growth. The bioactive agents may include, for example, bone morphogenic proteins, stem cells, blood, blood elements, bone marrow and bone marrow extracts, platelets and platelet extracts, homogenates of skin and skin homogenate extracts, growth factors, selenium and transferrin, calcium salts, and CYMETRA™ (CYMETRA™ is a registered trademark of LifeCell Inc., New Jersey).

"Bone formation," as used in the present invention, refers to the act of the bone-forming cells taking the form of bone cells, bone, cartilage, osteoids, and bone matrices.

The term, "bone material composition," means a composition comprising the bone fibers or bone fibers plus anorganic or inorganic components mixed with the bone fibers of the present invention and bone-forming cells. Typically, this combination has physical characteristics that allow infusion of visous materials such as bone marrow and osteoinductive effect so as to allow the bone-forming cells to form into new bone cells under appropriate conditions.

The "cutting cycle" is a single forward plus backward stroke of the cutter across the substrate as disclosed herein.

A "cutting event" is the complete cutting run of a load chute of a substrate.

"Demineralization" refers to the act of removing minerals from tissues containing minerals. The demineralization may be conducted by processes known in the art.

The "fiber bone" or "bone fiber" of the present invention is the fiber made from bone by shaving or cutting along the length of the bone to provide the bone fiber its textured surface to which bone-forming cells may bind and the induction of bone growth may be initiated under appropriate conditions.

"Osteoinductive" shall mean the ability to induce or promote the formation of new bone either in vivo or in vitro. For example, the bone fibers of the present invention have been found to induce or promote the formation of new bone by bone-forming cells attached to its surface. The induction of new bone may be fostered by the presence of bioactive agents that assist in the initiation of this induction process.

The "substrate" of the present invention may be any material, i.e., non-biological or biological materials, which may be cut using the cutting device of the present invention.

Where the substrate is bone, for example, the bone fibers act as a material upon which an organism such as bone-forming cells may grow or attach.

II. Bone Fibers and Methods of Inducing Bone Formation

Figure 2A:
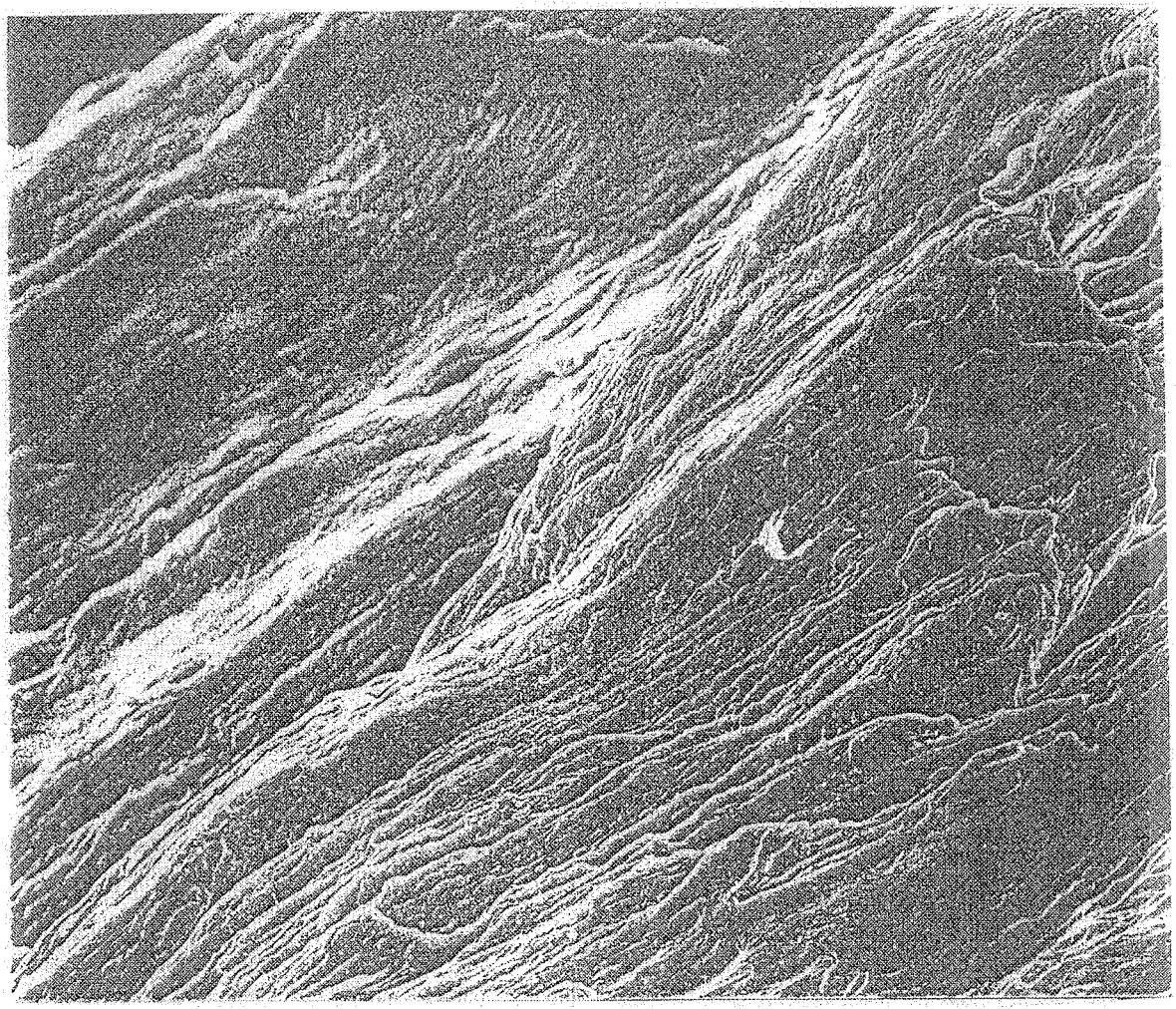
FIGS. 2A, 2B and 2C illustrate scanning electron photomicrographs of rehydrated bone fibers at a magnification of 268×.
Figure 2B:
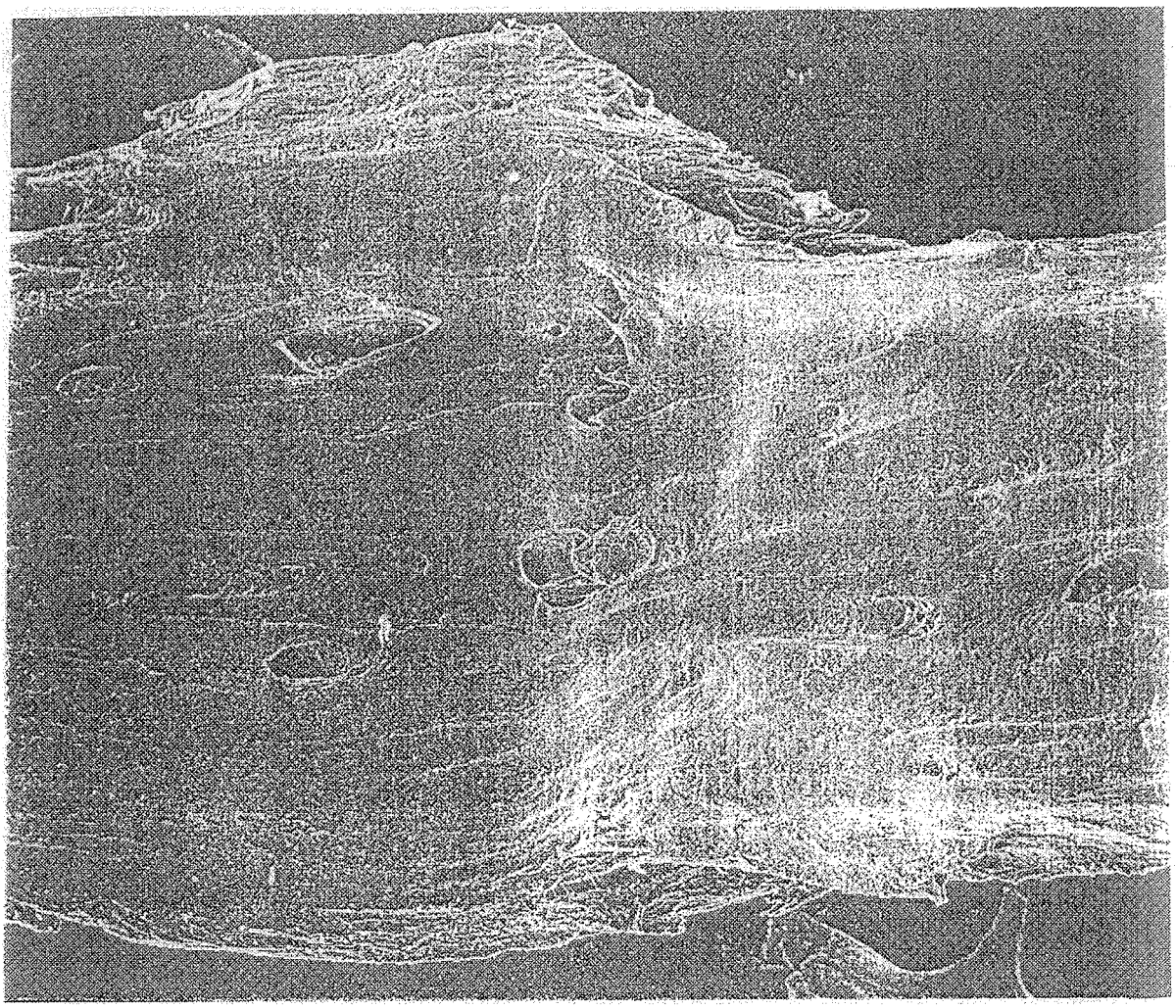
Figure 2C:
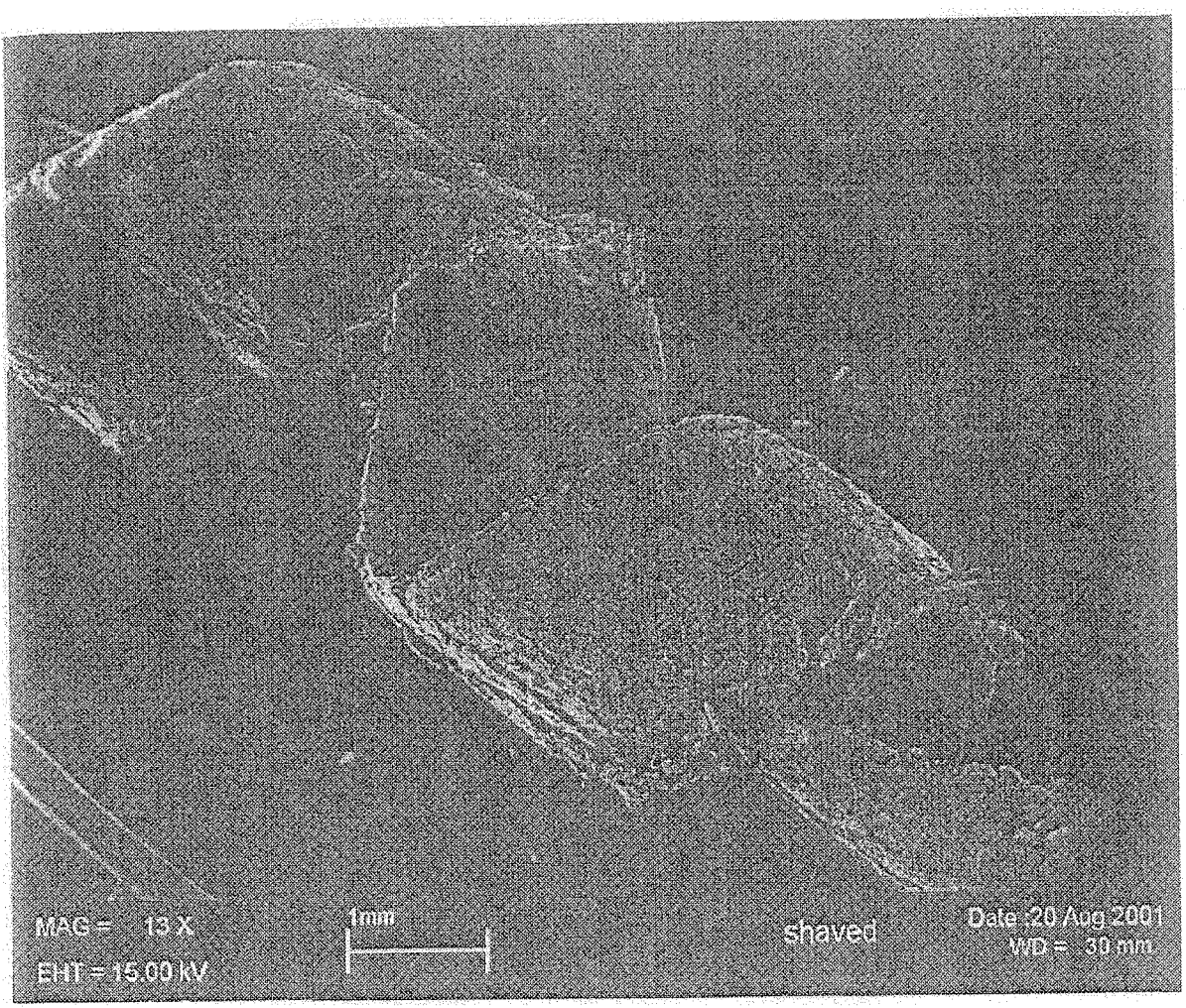

The bone fibers of the present invention have the ability to induce or promote bone formation and have properties particularly suitable as a component in bone implants. The bone fibers can be made from cortical or cancellous bone, and from any source, i.e., allograft or xenograft, by the essentially linear cutting from a bone-cutting device. The essentially linear cuttings, i.e., cuttings along the grain direction of the bone, result in bone fibers that optionally curl with the cutting process to form ribbon-like structures such as shown in FIG. 1. The fibers of the present invention preferably have a textured surface, as shown in FIGS. 2A, 2B, and 2C, having serrated edges and grooves as well as parallel striations, which provide an improved binding substrate to which bone-forming cells may attach. It is believed that this textured surface provides more available attachment sites to which bone-forming cells may adhere. Upon attachment, these cells can differentiate to form new bone and proliferate as new bone cells. Thus, the fibers of the present invention enhance the ability of bone-forming cells to bind to them so as to enhance the formation of new bone.

Fibers can be cut from any substrate that is capable of being cut using the device. Suitable substrates include non-biological materials, and biological materials. For example, suitable substrates include bone, bone tissue, plasticized bone, plasticized soft tissue, freeze-dried bone, freeze-dried soft tissue, frozen bone, frozen soft tissue, newly formed bone, implant bone, and associated cells, bone marrow, bone marrow-like tissue, cartilage, and cartilage-like tissues. Preferably, the substrate is bone tissue. Any type of bone may be used, such as allogenic and xenogenic bone. The bone tissue may be derived from any mammalian source, but is preferably human.

Production of bone fibers begins with the procurement of bone suitable to the preparation of fiber bone and includes any bone in an animal, such as bone diaphyseal shafts of long bones, for example the femur, tibia, humerus, ribs, radius, fibula. In humans, such bones are composed primarily of cortical bone tissue, but may also include cancellous bone.

The bone used to make the bone fibers may be processed in known manners prior to forming the fibers of the present invention. For example, the bone may be treated with enzymes to partially digest the organic components of the bone, such as collagenase, papain, protease, hyaluronidase, endonuclease, lipase, and/or phosphatase, or organic acids, such as acetic or citric acid. Alternatively, the bone may be partially digested by breaking or fragmenting the covalent bonds in the individual collagen molecules contained in the demineralized bone. Once the bone is cleaned of associated soft tissue, it can then be optionally cut into lengths and shapes appropriate for use in the cutting device. Alternatively the fiber bone can be cut directly from the shaft portions where the cutting blade can be attached to a manual (hand-held) cutting blade holder.

The bone tissue is used to form the bone fibers by contacting the bone tissue with an instrument capable of cutting along the length or along the grain direction of the bone tissue. The cutting instrument should be capable of cutting to provide serrated edges and grooves on the resulting bone fibers, which act as a surface-enhanced binding substrate for bone-forming cells. It has been found that bone-forming cells have an increased ability to attach to these bone fibers. While not intending to be bound by particular theory, it is believed that the edges and grooves formed on the bone fibers of the present invention provide more attachment sites to which the bone-forming cells may bind.

Cell binding to the fiber bone may be easily observed and quantitated using any number of assay methods known in the art. For example, cell populations present in any number of suspension formats, for example, bone marrow, concentrated platelets, blood, liver homogenates, etc., can be incubated with the fiber bone. The fiber bone can then be separated from the cell solution(s), gently washed to remove loosely adherent cells and other biomaterials present in the cell suspensions. The cells retained on the fiber bone can be quantitated using the traditional methyltetrazolium (MTT) assay where an insoluble chromogenic compound is formed due to the presence of metabolically viable cells (active mitochondrial enzymes) where fiber bone incubated with the suspension format lacking cells is used as a control. Alternatively, the fiber bone can be fixed with any number of fixatives, for example, formalin, and the DNA in adherent cells stained for visualization using light microscopy. The phenotypic identity, for example, fibroblasts, chondroblasts, osteoblasts, etc. can be verified using traditional enzyme assays such as alkaline phosphatase activity stains. Fibroblasts (less differentiated cells) stain only minimally for this enzyme, whereas chondrogenic and osteogenic cells stain heavily for this enzyme.

In the method of inducing new bone formation, the bone fibers of the present invention may be used in either a mineralized or demineralized state or a combination thereof. Whether mineralized or demineralized, the bone fibers have the textured surface to which the bone-forming cells may efficiently attach. In the case of demineralized bone fibers, the ribbon-like structures typically unwind into essentially linear strips of bone.

The bone fibers may be of any length, width, and thickness as deemed necessary or useful for its intended use. For example, the fibers may be the length of bone tissue from which they are being made. Alternatively, the fibers may be designed to be cut at shorter lengths to accommodate their use in particular bone implants. Bone fibers preferably have average length of from about 1 mm to about 100 mm, an average width of from about 0.5 mm to about 2.5 mm, and an average thickness of from about 0.2 mm to about 1.4 mm, more preferably having an average length of from about 20 mm to about 30 mm, an average width of from about 1.0 mm to about 2.0 mm, and an average thickness of from about 0.4 mm to about 0.8 mm. Furthermore, it is noted that the length of the fibers produced according to the invention may be substantially greater than the width and thickness of the fibers. For example, the bone fibers may have a length that is greater than about 10 to about 200 times its width and thickness, preferably about 40 to about 100 times its width and thickness. As will be described further herein, the cutting apparatus of the present invention may be modified to accommodate any desired length, width or thickness of the fibers.

For demineralization, the mineral content of the bone fibers may be removed using any known process for demineralization causing the bone fibers to be demineralized. Preferably, the bone fibers are demineralized to contain calcium at a level of from about 0.5 wt % to about 4.5 wt %, more preferably from about 1.0 wt % to about 4.0 wt %, and most preferably from about 1.5 wt % to about 3.5 wt %, for example, as disclosed in U.S. Pat. Nos. 6,189,537 and 6,305,379; and co-pending U.S. patent application Ser. Nos. 09/655,711 and 10/180,989, the disclosures of which are herein incorporated by reference in their entireties. Once demineralized, the bone fibers may optionally be combined with agents including for example, biological carriers, bioactive agents, or other agents including for example, surface active agents, preservatives including for example glycerol, and inorganic mineral compositions, either before or after further processing, such further processing including but not limited to, freeze-drying, terminal sterilization processes, and/or retaining as a hydrated fiber bone in the presence or absence of preserving agents, or combined immediately prior to implantation in a patient. Moreover, the bone fibers of the present invention may be further combined with other carriers and agents as one having ordinary skill in the art would appreciate for the use DMBs. For example, suitable biological carriers include collagen, gelatin, saccharides, fibrin, fibrinogen, alginates, hyaluronins, methylcelluloses, and biologically compatible thixotropic agents. Suitable bioactive agents include but are not limited to, bone morphogenic proteins, stem cells, blood, blood elements, bone marrow and bone marrow extracts, platelets and platelet extracts, homogenates of skin and skin homogenate extracts, growth factors, selenium and transferrin, calcium salts, and CYMETRA™.

Production of demineralized bone biomaterials and the induction of new bone by these biomaterials are described in U.S. Pat. Nos. 5,275,954, 6,189,537 and 6,305,379, of which are herein incorporated by reference in their entireties. The bone fibers of the present invention may induce or promote new bone formation by serving as a source of one or more chemoattractants that diffuse from the bone biomaterials to cause cells to migrate to the implanted bone fibers wherein cells adhere to the bone particles (normal mammalian cells are "attachment dependent," meaning they typically require attachment to some surface in order to function metabolically) and differentiate towards a chondrocytic (cartilage forming) or osteocytic (bone forming) phenotype. In accordance with the present invention, it is believed that surface characteristics of the bone fibers of the present invention render the fibers more accessible and are a more accepting substrate to receive and bind bone-forming cells. Thus, the surface characteristics of the bone fibers may result in improved cell attachments, and consequently, act as a means for selectively attaching cartilage or bone-forming cells from a mixed population of cells, such as are present in platelet-rich plasma, blood, blood products, or bone marrow.

In accordance with the present invention, the surface patterning present on the bone fibers preferably contains parallel striations, cracks, and serrated edges and grooves to which cells may attach. This surface pattern of the bone fibers of the present invention permits a multitude of cells to bind to the bone fibers allowing less specific cells to bind and grow based on the functional properties of the fibers.

In a preferred embodiment of the present invention, the surface patterning of the bone fibers is created by the bone-cutting device of the invention as described herein. As illustrated in FIGS. 2A, 2B, and 2C, the cutting "bits" (blades) of the fiber bone-cutting device cause a microfractured surface with specific patterns of parallel surface striations on the cut surface of the fiber bone. Thus, in addition to the normal osteoinductive properties of demineralized bone (as described in U.S. Pat. No. 6,189,537), the bone fibers of the present invention, whether demineralized or not demineralized, present a micro-patterned surface that is not only biocompatible with bone-forming cells; but also presents a surface conducive to cellular attachment, cell spreading, and cell proliferation/differentiation (or maintenance of phenotype of an already differentiated cell). The available surface area of fiber bone produced by the present fiber bone cutting device, as compared to normal particle bone (produced by impact fragmentation), is greater, is biocompatible, and presents the surface patterning conducive to cellular attachment, proliferation, and differentiation. Due to the individual and multiple cutting bits present on a cutter present within the fiber bone cutting device, the multiplicity of patterns on the multiple fiber bone fibers produced would contribute to maximal availability of optimal surface patterning for cellular attachment. Thus, the fibers of the present invention can have variable sizes, spacing between striations, depths, density, and orientations. Preferably, the fibers are cut along the grain to obtain a greater durability of the fiber.

The "bone-forming cells" or "bone-matrix forming cells" of the present invention are those cells suitable for the induction of new bone formation when infiltrated with the bone fibers of the present invention and include those cell types suitable for differentiating into bone cells or suitable for forming a matrix similar to osteoid of forming new bone. Suitable cell types may include differentiated, partially differentiated, or undifferentiated cells. For example, cell types include, but are not limited to stem cells, connective tissue progenitor cells, fibroblast cells, periosteal cells, chondrocytes, osteocytes, pre-osteoblasts, and osteoblasts. Preferably, the stem cells are multipotent, the fibroblast cells are undifferentiated, the periosteal cells are partially differentiated, and the chondrocytes or osteocytes are differentiated.

Preferably, the bone-forming cells are stem cells. Stem cells represent a population of cells present throughout the body of mammals that are undifferentiated possessing the potential for differentiating into virtually any other, more differentiated, cell in the body. For this reason, stem cells represent a unique opportunity to repair and/or remodel damaged tissues such as broken bones, abraded cartilage, skin, etc.

Moreover, the bone-forming cells may be tissue progenitor cells. For example, U.S. Pat. Nos. 5,824,084 and 6,049,026 (and U.S. patent application 2002/0161449) describe kits and composite bone grafts contained in the kits, wherein the composite bone graft(s) are designed to contain an enriched population of connective tissue progenitor cells and a greater number of connective tissue progenitor cells per unit volume than found in the original bone marrow aspirate.

In one aspect of the invention, the bone fibers of the present invention allow for the formulation of "bone material compositions" comprising the bone fibers for use in bone implants. These bone material compositions provide increased accessibility of the bone fibers to bone-forming cells by permitting suitable voids through which viscous solutions of platelet rich plasma, bone marrow, blood or blood products may flow. For example, the bone fibers may be demineralized and compacted to form a bone material composition suitable for implantation. Because the bone fibers of the present invention are easily handled without breaking apart, the bone fibers may be molded to create an implantable composition, which retains its shape in the implant and further has appropriate spacing through which such solutions comprising bone-forming cells may pass. These bone material compositions may further have integrated therein other components, such as inorganic particles, organic particles, or more specifically non-demineralized cancellous or cortical bone chunks, which may increase the ability of such solutions to flow through the composition by providing structural spacing of the fiber bone. Under such conditions, the surface of the fiber bone fibers would be presented to the infiltrating bone marrow/platelet rich plasma preparations to promote cellular attachment, selectively concentrating the cells most appropriate to the formation of bone or cartilage when the bone material composition is then implanted into some clinical site in the body. Such ex-vivo exposure of the bone fiber biomaterials to osteogenic or chondrogenic cells would serve to concentrate cells that would normally be expected to migrate into the implanted materials through the normal chemoattractive properties of demineralized bone. Thus, this pre-implantation exposure of cells to the bone fibers should reduce the time required for the initiation of new bone formation and lessen the clinical times needed to affect a repair of the damaged site in the body, i.e. a broken bone or fusion site in an intervertebral fusion procedure for repair of cervical or lumbar complications in the spine. Other suitable components for integration into the bone material include, but are not be limited to, inorganics such as particulate calcium salts, such as calcium phosphates, calcium sulfates, and/or calcium carbonates, organics such as particulate skin, particulate cartilage, particulate tendons and ligaments, particulate dextrans, particulate alginates, and particulate resorbable and non-resorbable synthetic polymeric materials.

The bone material compositions may be formed in manners known in the art. In one embodiment of the present invention, the bone fibers of the present invention and bone-forming cells are preferably placed in a bioreactor capable of simulating the nutrient flow and waste removal present within an implant site. The flow of nutrient solutions into, through, and out of the bioreactor permit the associated ground demineralized bone and bone-forming cells to form into bone or bone-like biomaterial suitable for transplantation. In the present instance, the bioreactor use aspect of the present invention would simulate the actions of the fibers and fiber bone compositions when used clinically. The process of making bone in a bioreactor is described in Application No. 60/466,772, for example, which is herein incorporated by reference.

In another aspect of the invention, the bone fibers of the present invention have exhibited superior properties for the formation of bone implants. Bone implants may be formed using the bone fibers of the present invention based on their ability to be easily handled for molding, retaining its shape, and allowing appropriate spacing for biological solutions to pass therethrough even upon compaction. For example, the fibers may be hydrated, which renders then pliable and malleable, but capable of retaining its shape without losing durability. In fact, the fibers have been shown to retain its integrity even upon hydration, molding, and subjection to other bone implant-forming treatments. Therefore, the bone fibers of the present invention have superior properties making them ideal for the formation of bone implants.

In another aspect of the invention, the bone fibers can be used alone or in conjunction with a bone material composition and placed in a suitable container through which blood, blood products, bone marrow, or platelet rich plasma can be induced to flow through such that the cells capable of adhering to the bone material composition, specifically the fiber bone, are suitably concentrated for implantation into a site in the body wherein the formation of new bone is desired.

III. Production of Bone Fibers

Figure 5:
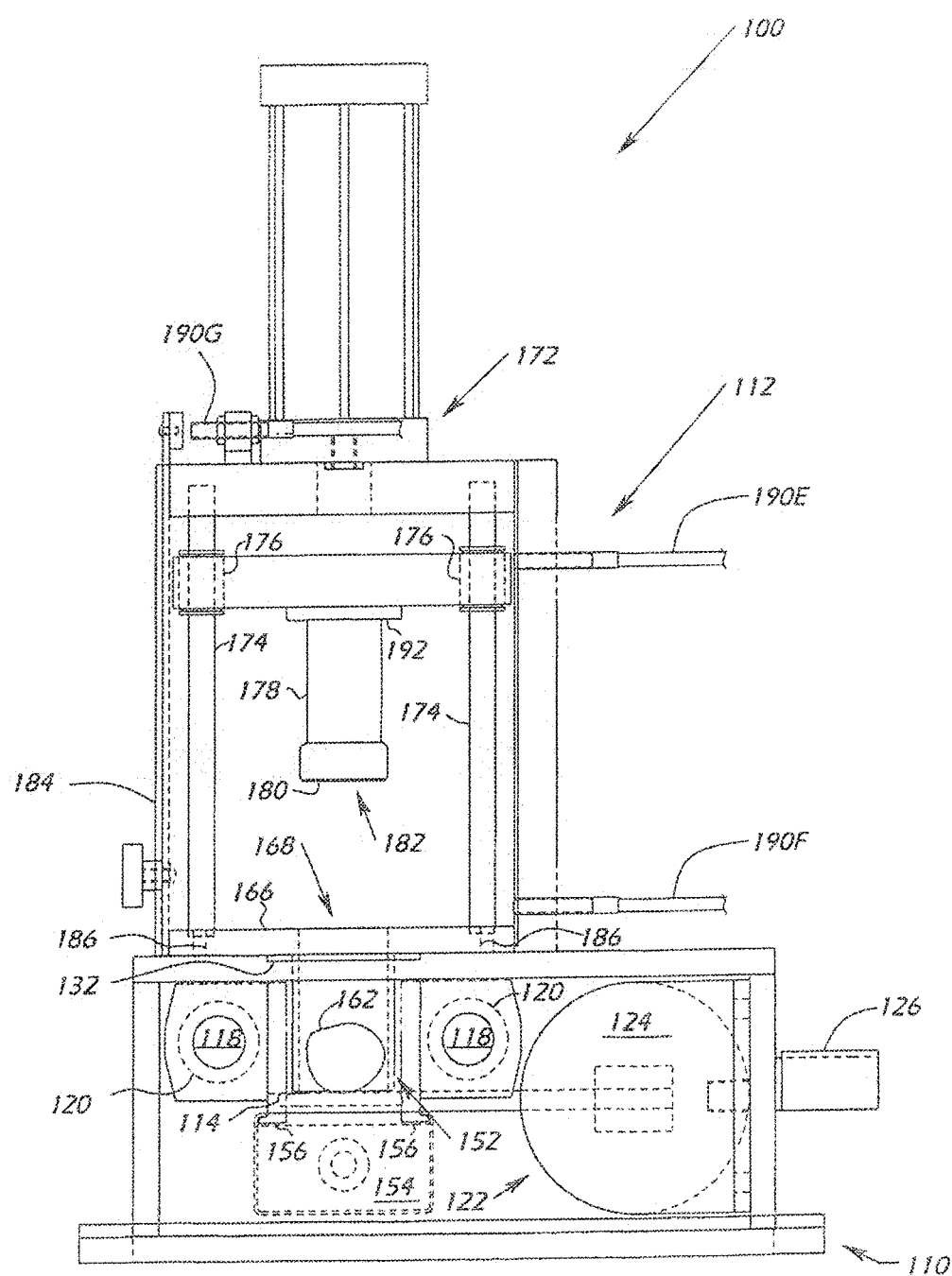
FIG. 5 is a side elevational view of a substrate cutting device according to an exemplary embodiment of the present invention.
Figure 14:
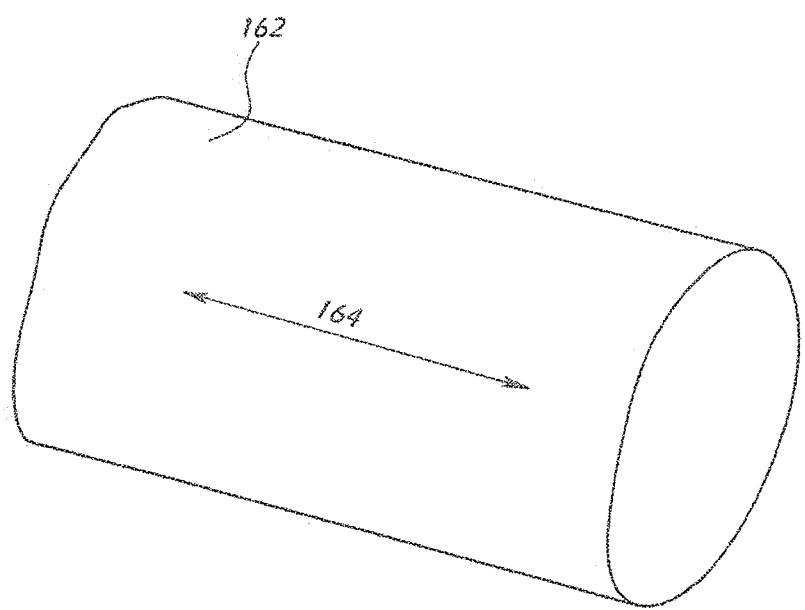
FIG. 14 illustrates an exemplary substrate.

Referring to FIG. 5, a device for cutting substrates in accordance with the present invention will now be described. The substrate cutting device 100 includes a base 110, a tower 112, and a cutter 114. With continued reference to FIG. 5 and additional reference to FIG. 6, the base 110 of the substrate cutting device 100 includes a slide mechanism 116 which travels along a predetermined cutting path. Preferably, the cutting path is along with, or substantially parallel to, a grain 164 (see FIG. 14) of the substrate being cut. A pair of guide rods 118 is used to control the direction of the slide mechanism 116 during operation. A plurality of bearings 120 are also used to slidably engage the guide rods 118.

Figure 6:
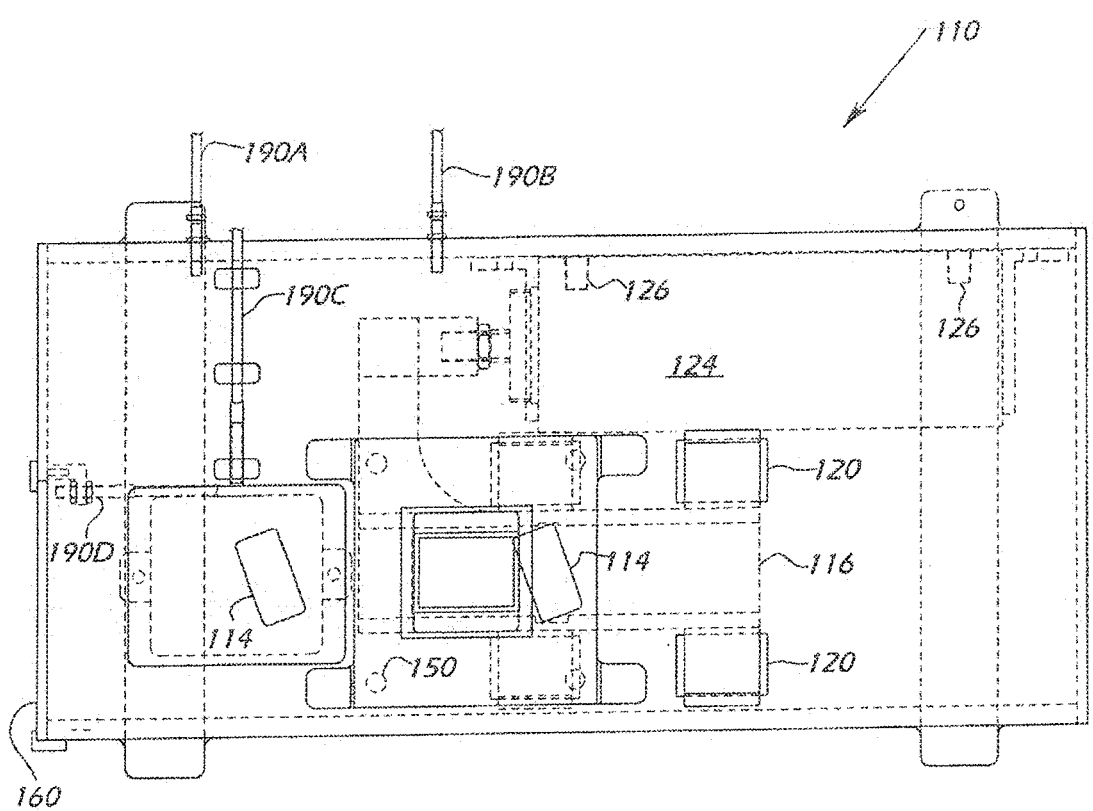
FIG. 6 is a top plan view of the substrate cutting device.
Figure 7:
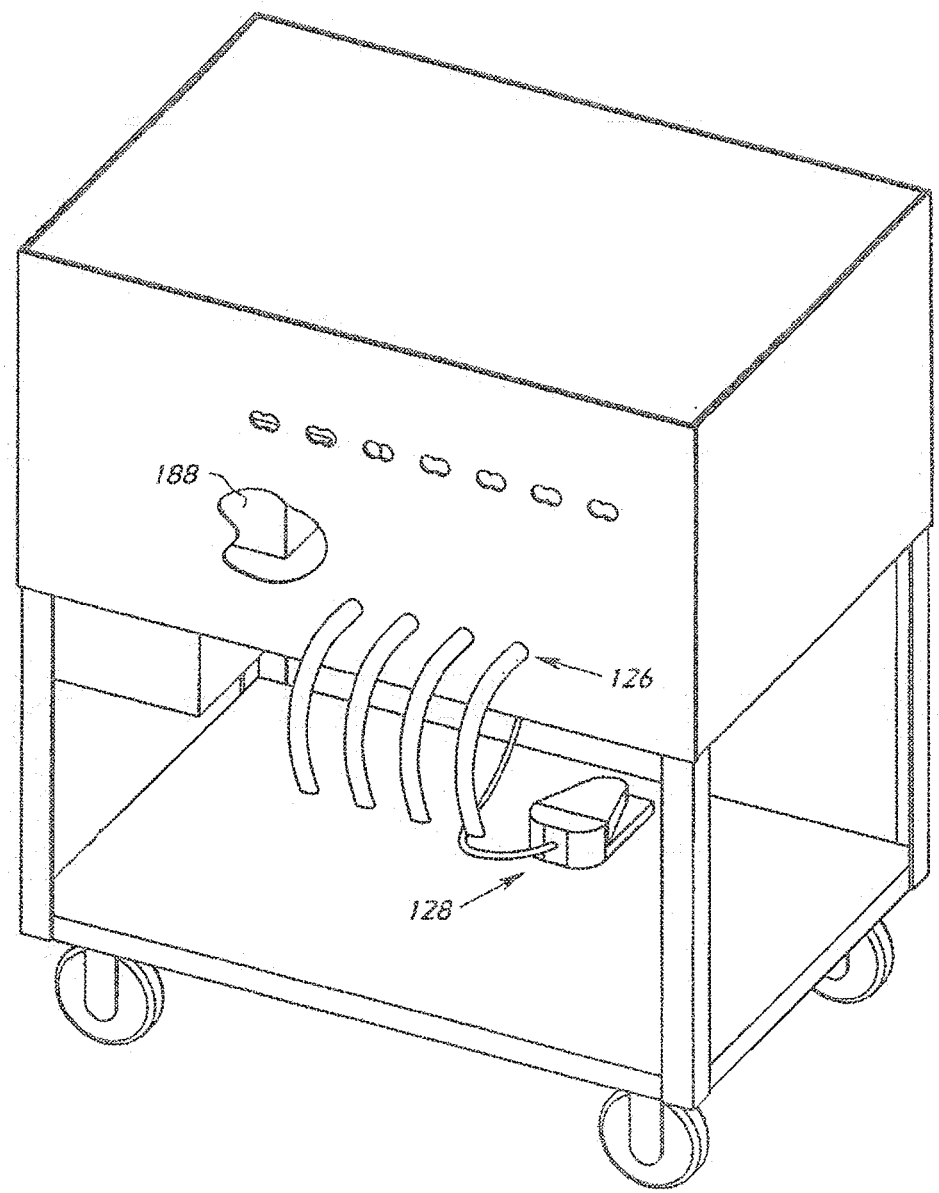
FIG. 7 illustrates an operations cart that can be used to support the substrate cutting device and store various components.

A first actuation unit 122 generates to force necessary to move the slide mechanism 116. According to the disclosed embodiment of the invention, the first actuation unit 122 is pneumatically operated. It should be noted, however, that the first actuation unit 122 can also be operated hydraulically, electrically, and/or mechanically depending on the specific requirements. As illustrated in FIGS. 5 and 6, the first actuation unit 122 includes an air cylinder 124 that receives pressurized air to generate the forces necessary for moving the slide mechanism 116. Referring additionally to FIG. 7, a plurality of pneumatic cables 126 are used to supply air to the air cylinder 124. Preferably, the air is pressurized at an external location and transferred to the substrate cutting device 100. According to such an arrangement, the pressurized air can optionally be processed in order to maintain sterile environment, when necessary. FIG. 7 also illustrates a foot pedal 128 which can be used to control the operation of the substrate cutting device 100. A computer controller 188 can also be provided to monitor and control operation of the substrate cutting device 100.

According to the disclosed embodiment of the invention, the first actuation unit 122 is configured to generate a force ranging from 600 lbs to 900 lbs. Preferably, the first actuation unit 122 generate a force ranging from 700 lbs to 800 lbs. Most preferably, the force is approximately 750 lbs. Additionally, the force can be varied during operation of the substrate cutting device 100, or it can be maintained at a constant level. For example, according to one embodiment of the invention, the computer controller 188 can be used vary the force applied by the first actuation unit 122 by reducing the amount of force applied during a return stroke and increasing the force applied during a cutting stroke.

Figure 8:
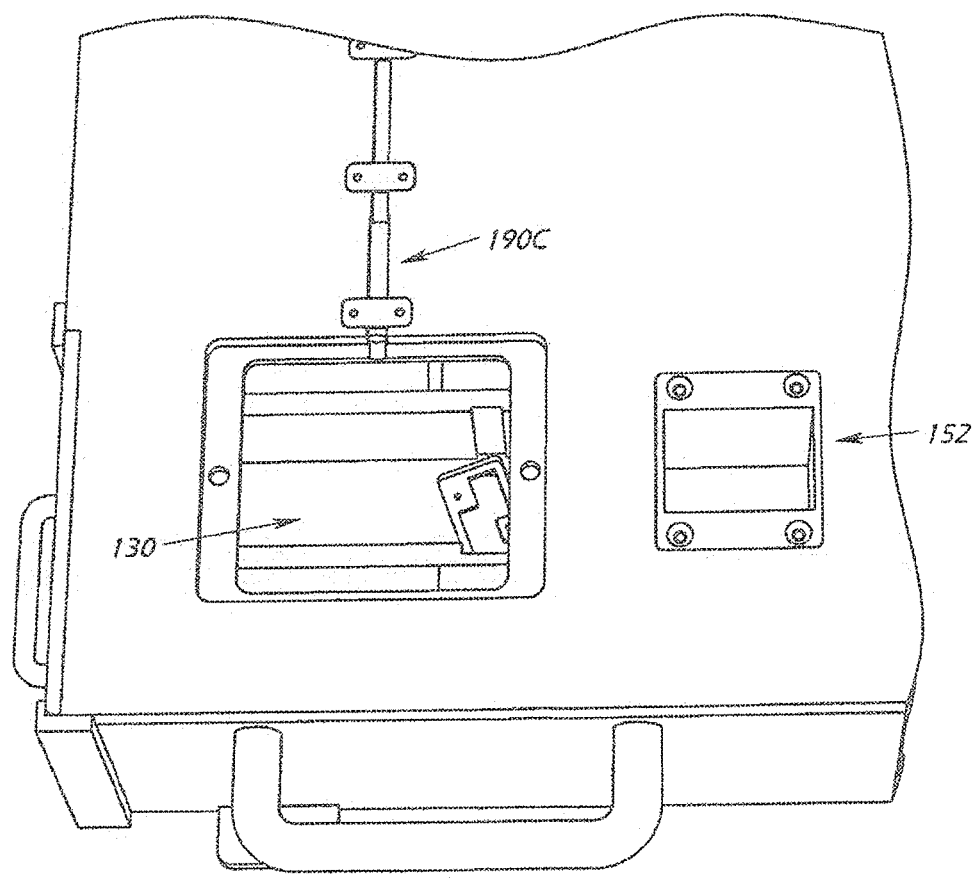
FIG. 8 illustrates a top portion of the base of the substrate cutting device.

As best illustrated in FIG. 8, the top surface of the base 110 includes a cutter access 130 which allows an operator to mount the cutter 114 within the substrate cutting device 100. The top surface of the substrate cutting device 100 also includes a substrate chute 152 designed to appropriately position a substrate 162 (see also FIG. 14) so that it may be engaged by the cutter 116. The dimensions of the substrate chute 152 can vary depending on the specific substrate and product desired. The various parts of the substrate cutting device 100 can be secured using a variety of means such as, for example, threaded fasteners 150 or any appropriate method capable of providing the strength and/or function necessary for proper operation. FIG. 8 also illustrates that the cutter 114 is rotated such that it is offset from the cutting path when mounted on the slide mechanism 116. The specific rotational offset can be selected based on a variety of factors including, but not limited to, the type of substrate, the specific arrangement of the blade sections on the cutter, and the amount of force being applied by the first actuation unit.

Figure 9:
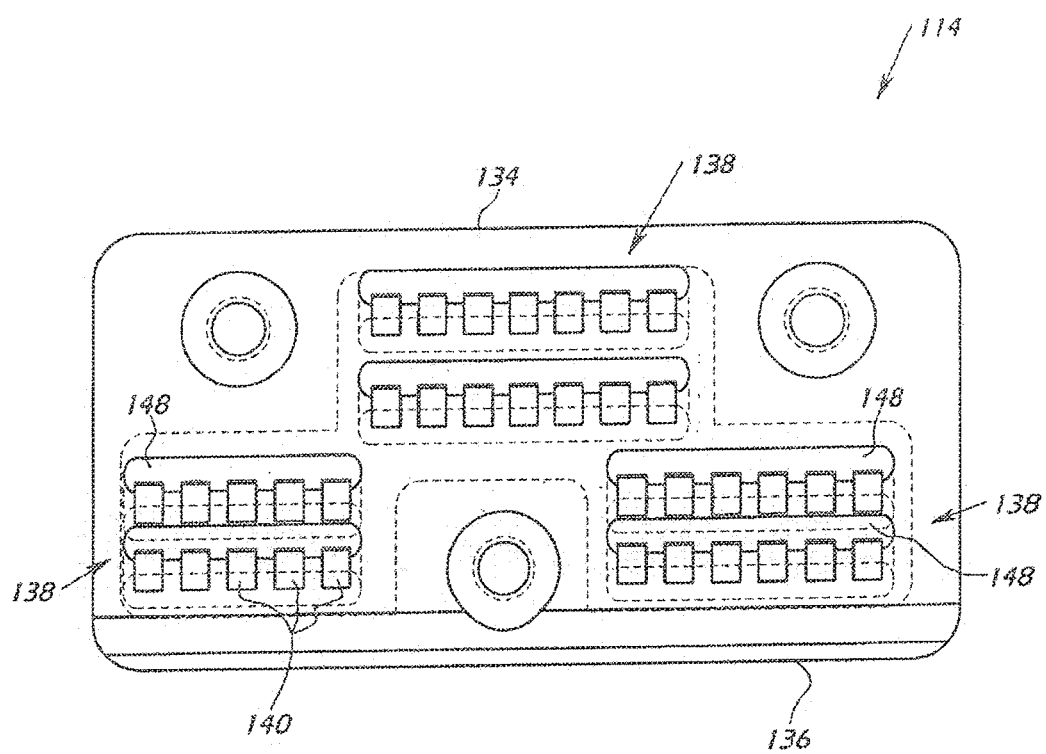
FIG. 9 is a top plan view of a cutter in accordance with an exemplary embodiment of the present invention.

Turning to FIG. 9, the details of the cutter 114 will now be described. The cutter 114 includes a leading edge 134 and a trailing edge 136. During a cutting stroke, the leading edge 134 is the first portion of the cutter 114 to reach the substrate 162. It should be noted, however, that the leading edge 134 will not necessarily contact the substrate 162. The cutter 114 includes a plurality of blade sections 138 disposed on its surface. Each blade section 138 contains two rows of teeth 140. Depending on the specific application, desired product, and substrate, the cutter 114 can include a single blade section 138 or multiple blade sections 138 (as shown in FIG. 9). Additionally, a single row of teeth, or multiple rows of teeth may be provided.

Figure 10:
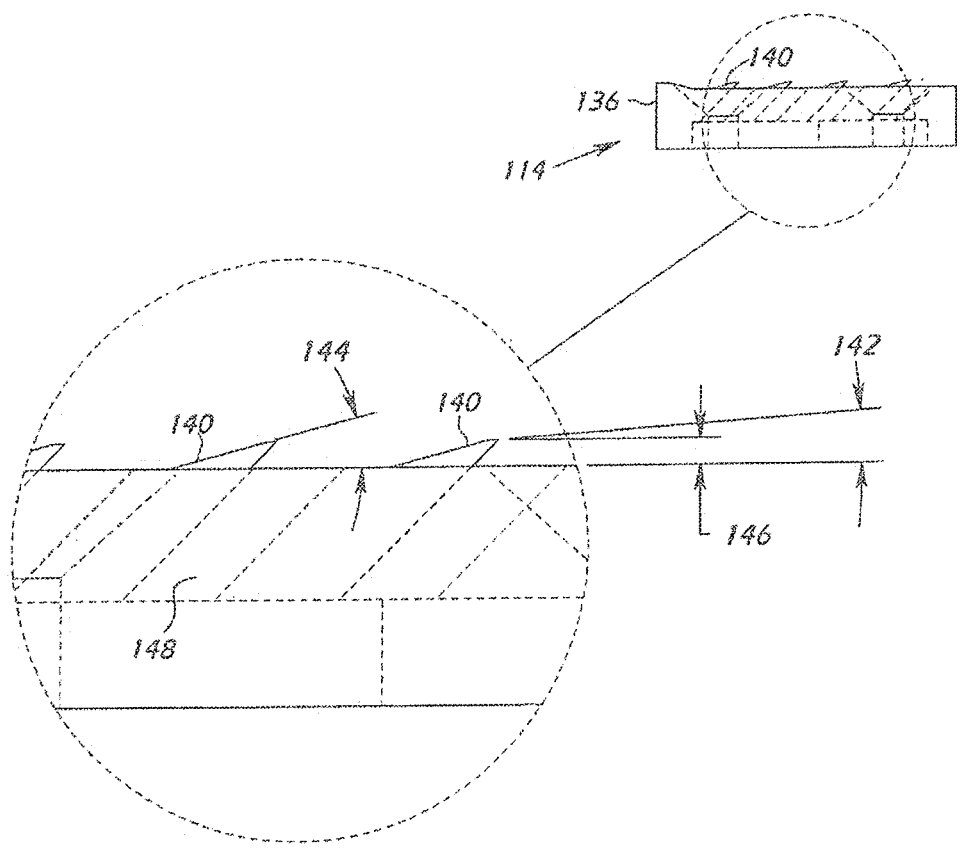
FIG. 10A is a side elevational view of the cutter.
FIG. 10B illustrates an exemplary configuration for the cutter teeth.
Figure 13:
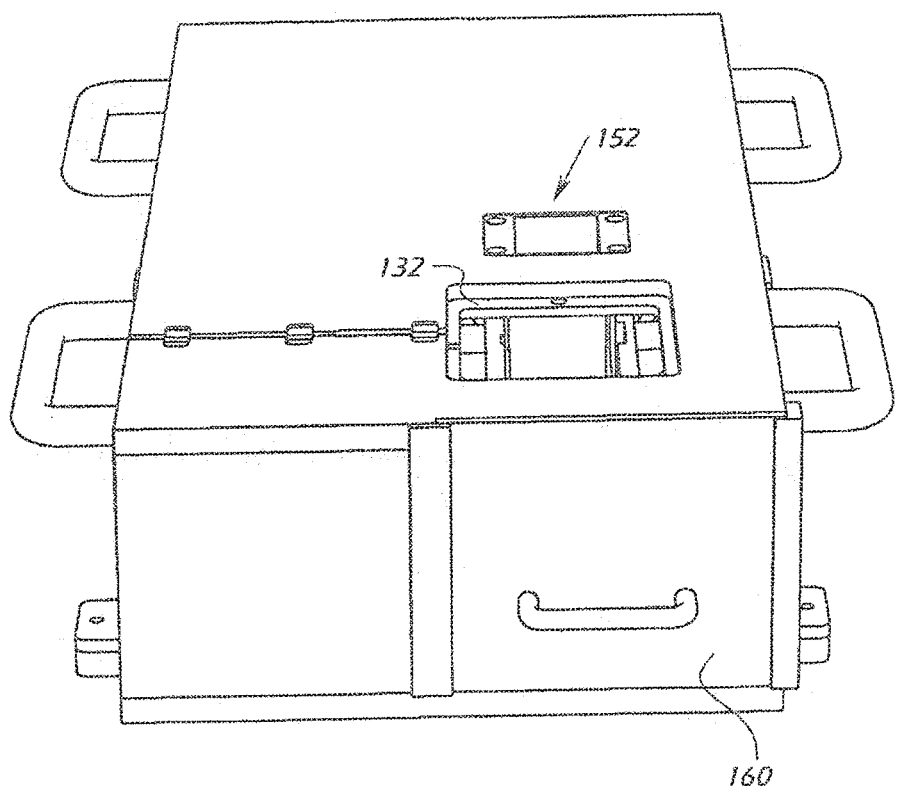
FIG. 13 illustrates the base of the substrate cutting device with all access doors in place.

According to the disclosed embodiment of the present invention, when the cutter 114 is mounted on the slide mechanism 116, the cutter surface is substantially flush with the surface of the slide mechanism 116. Such a configuration advantageously minimizes movement of the substrate 162 during operation. Furthermore, as shown in FIG. 10A, the trailing edge 136 of the cutter 114 is raised by a predetermined amount. Preferably, this predetermined amount is approximately equal to the height of the teeth 140 in the blade section 138 in order to further minimize possible movement of the substrate 162 during operation. Referring additionally to FIG. 13, once the cutter 114 has been securely mounted to the slide mechanism 116, a cutter access door 132 is used to prevent access to the cutter 114 during operation of substrate cutting device 100.

Referring to FIGS. 10A and 10B, each tooth 140 in the blade sections 138 can include one or more cutting angles. In addition, the cutting angle can be independently selected for each individual tooth 140. More particularly, one tooth may include a single cutting angle while an adjacent tooth can include two cutting angles, and yet another adjacent tooth can contain three cutting angles. As disclosed in FIG. 10B, each tooth 140 contains a primary cutting angle 142 and a secondary cutting angle 144. The primary cutting angle 142 can be selected to be in the range of 3 to 6. Preferably, the primary cutting angle 142 is selected to be approximately 4.

The secondary cutting angle 144 can be selected in the range of 10 to 18. The secondary cutting angle 144 can also range from 12 to 16. Preferably, however, the secondary cutting angle 144 is selected to be approximately 14. FIGS. 10A and 10B also illustrate a cutting height 146 for the teeth 140. The cutting height 146 can vary depending on the specific operation and/or product desired. For example, the cutting height 146 can be used to define the thickness of fibers produced. The cutter 114 also includes a plurality of fiber channels 148 to allow passage of substrate fibers after being cut. The fiber channels 148 can be generally selected to correspond with the number of blade sections 138. More particularly, the cutter 114 is designed such that the cut substrate fibers pass directly through the fiber channel 148. Furthermore, the fiber channel 148 can be sized to assist in the production of substrate fibers having required features for a particular product. For example, by selecting an appropriate width for the fiber channel 148, the cut fibers can be prevented from curling back into the fiber channel 148 and possibly breaking prematurely. Likewise, selection of an appropriate depth for the fiber channel 148 can prevent fibers from curling into adjacent fiber channels 148.

Figure 11:
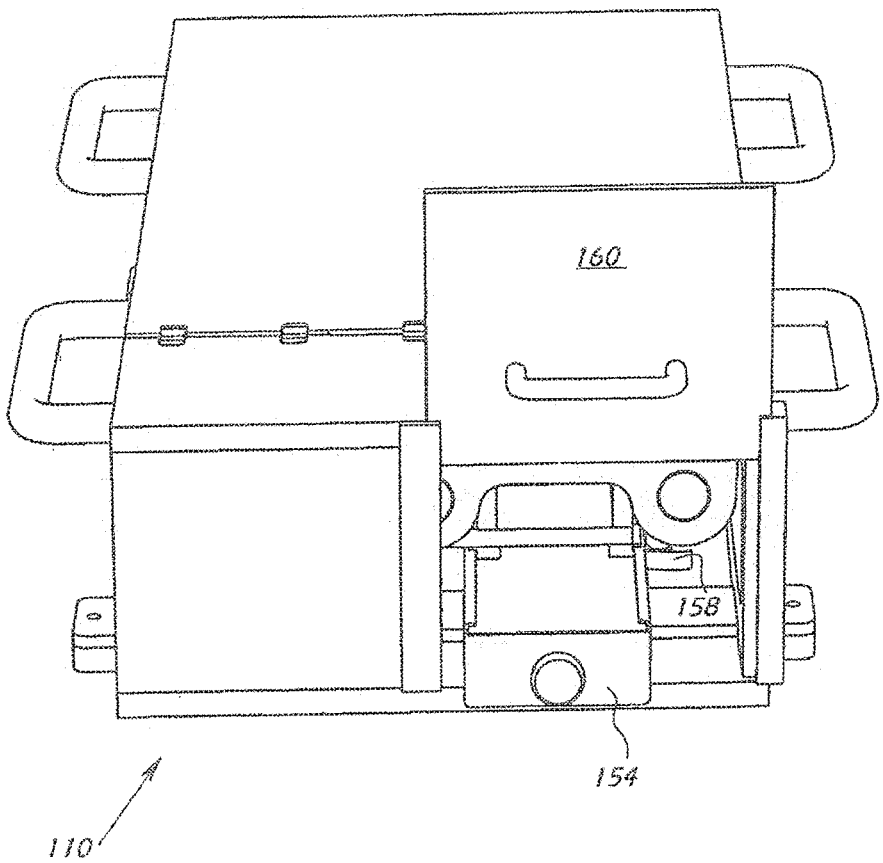
FIG. 11 is a perspective view of the base of the substrate cutting device.
Figure 12:
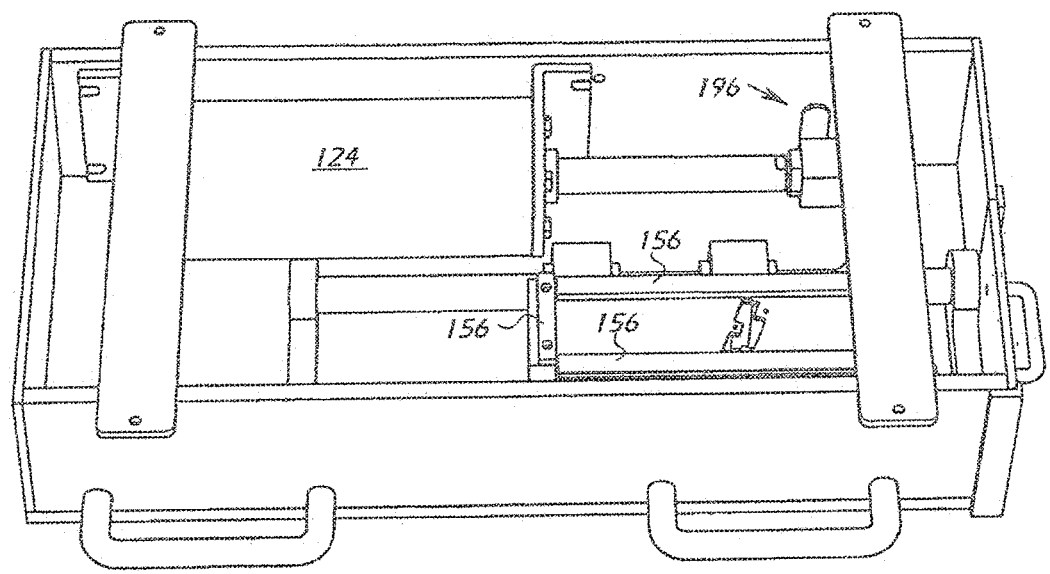
FIG. 12 is a top perspective view of a bottom portion of the base.
Figure 16:
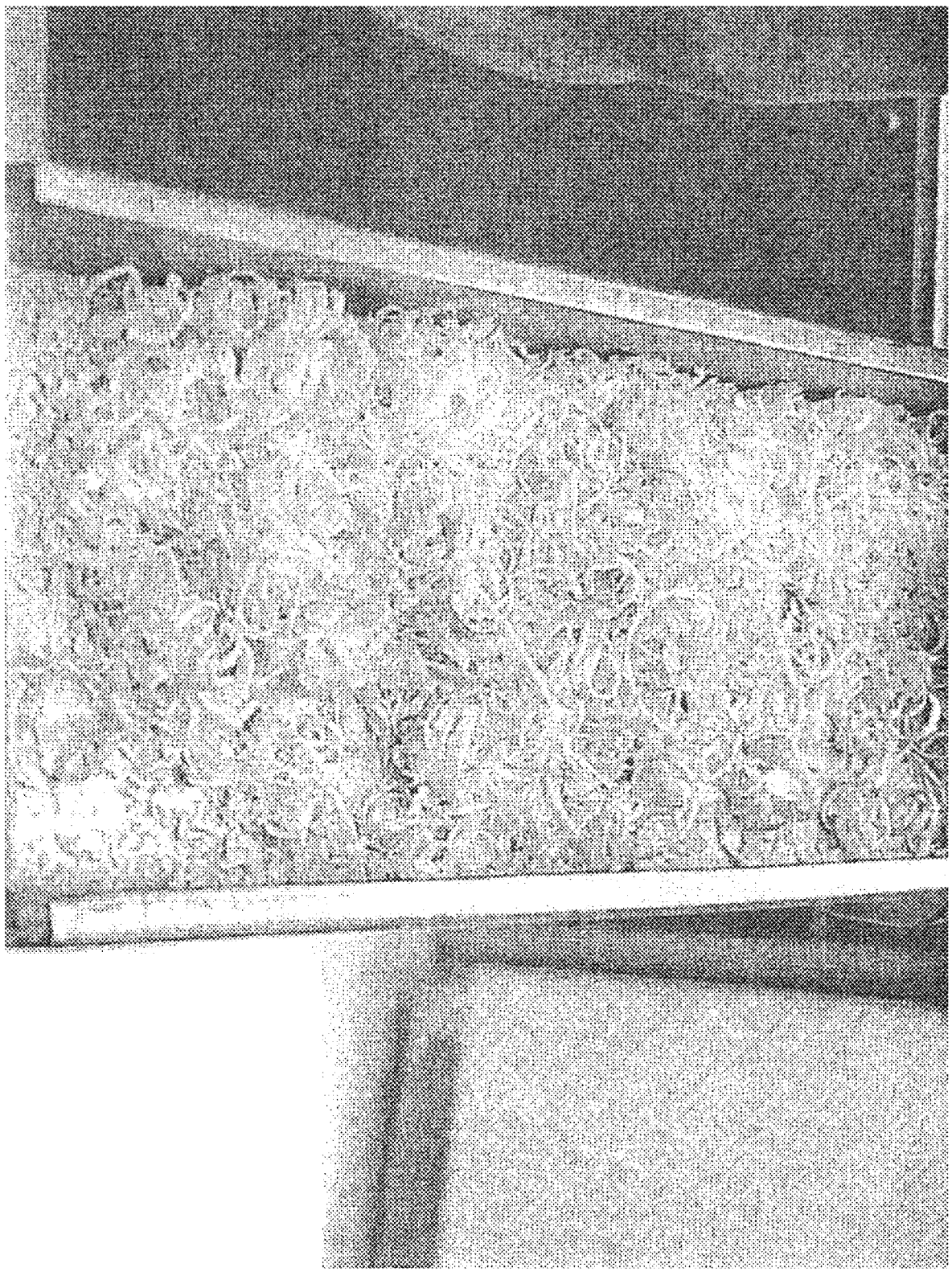
FIG. 16 illustrates substrate fibers produced according to one embodiment of the present invention.

Turning now to FIGS. 11 and 12, additional features of the base 110 will be discussed. The substrate cutting device 100 can include a fiber receptacle 154 for collecting substrate fibers that have been cut. FIG. 16 illustrates a plurality of fibers that have been collected in the fiber receptacle 154. The fiber receptacle 154 is inserted into the base 110 such that it is aligned with the cutter 114 and the fiber channels 148. Accordingly, the cut fibers will fall directly into the fiber receptacle 154. A plurality of guides 156 (best seen in FIG. 12) are provided to properly align the fiber receptacle 154. A locking clip 158 can optionally be used to secure the fiber receptacle 154 in place. It should be noted, however, that various other methods and arrangements can be used to secure the fiber receptacle 154 in place. A receptacle door 160 is used cover the fiber receptacle 154 and prevent access during operation of the substrate cutting device 100. The receptacle door also includes a reflector (not shown), such as the reflector 196 on the slide mechanism 116, that allows sensor device 190d to determine whether the receptacle door 160 is closed.

Turning again to FIG. 6, the base 110 includes a plurality of sensor devices 190(a-d). The sensor devices 190 are preferably optical, but can incorporate various other detection methods as is well known. Sensor device 190a detects when the slide mechanism 116 has reached the rest (or home) position. Sensor device 190b detects when the slide mechanism 116 has completed the cutting stroke. Sensor device 190c detects the presence of the cutter access door 132. As previously indicated, sensor device 190d detects the presence of the receptacle door 160. Under normal circumstances, if sensor devices 190c and 190d return a fault, then operation of the substrate cutting device 100 is immediately halted. Additionally, sensor devices 190a and 190b can be used to monitor movement of the slide mechanism 116.

Figure 15:
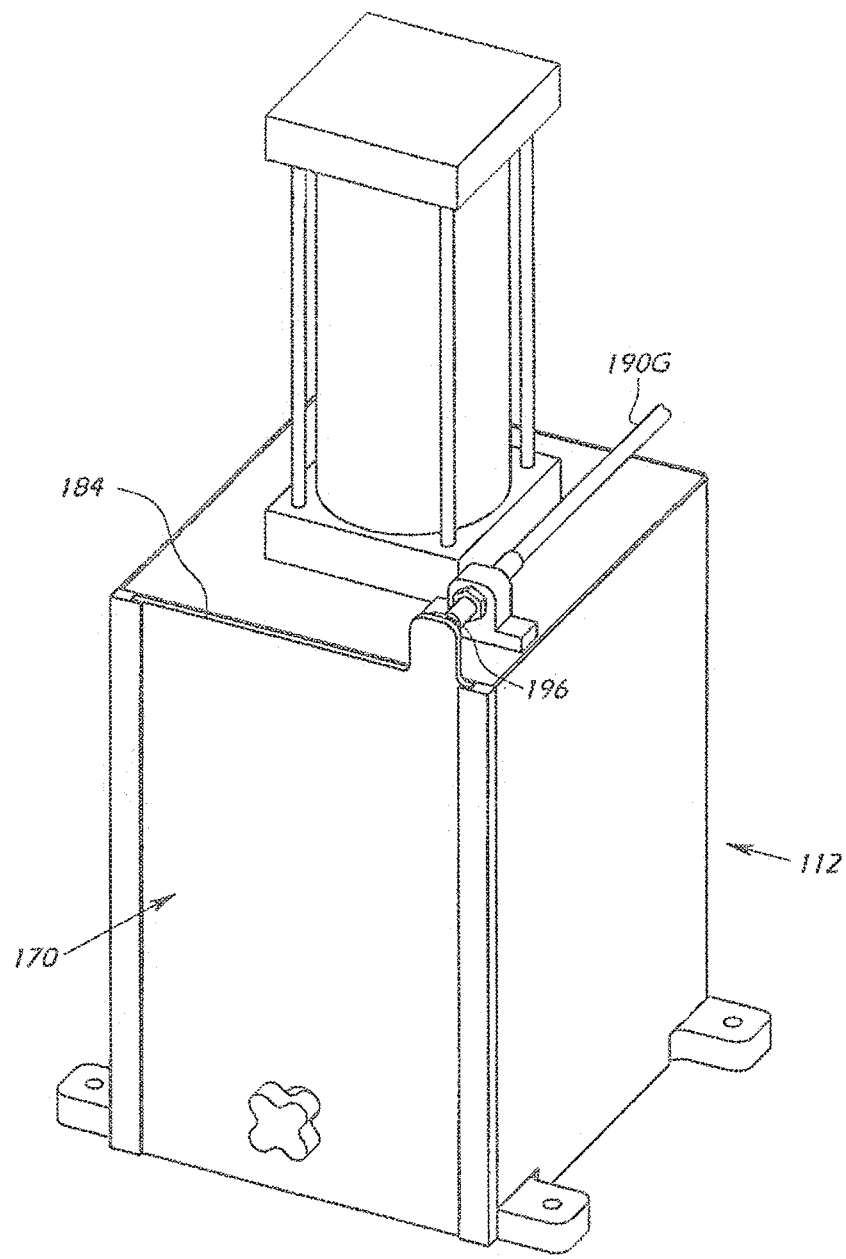
FIG. 15 is a perspective view of an exemplary tower for use with the substrate cutting device.

Referring to FIG. 15, with additional reference to FIG. 5, the tower 112 includes a lower surface 166 having a recess 168 therethrough. The recess 168 is positioned such that it can be aligned with the substrate chute 152. The tower 112 includes an opening 170 on a front portion thereof. The opening 170 is used to allow placement of the substrate 162 within the substrate chute 152. Once the substrate 162 is in placed in the substrate chute 152, a clamping mechanism 178 is used to keep the substrate 162 in contact with the cutter 114.

A second actuation unit 172 is used to generate the force necessary to operate the second actuation unit 172. As illustrated in the embodiment of the invention shown in FIG. 5, the second actuation unit 172 is pneumatically controlled. It should be noted, however, that hydraulic, mechanical, electrical, and other control systems can be used, so long as they are capable of supplying the force necessary to operate the clamping mechanism 178. According to the disclosed embodiment of the invention, the second actuation unit 172 is capable of generating a force ranging from 150 lbs to 250 lbs. Preferably, the second actuation unit 172 generates a force of approximately 200 lbs. Similar to the first actuation device 122, the force can be varied during operation of the substrate cutting device 100 or it can be maintained at a constant level. Additionally, the computer controller 188 can be used to monitor and/or vary the force applied by the second actuation unit 172.

As shown in FIG. 5, the clamping mechanism 178 includes a contact surface 180 that engages the substrate 162. According to a preferred embodiment of the invention, the contact surface 180 contains a plurality of grooves 182 designed to increase the friction force between the clamping mechanism 178 and substrate. The tower also includes a door 184 which prevents access during operation. One or more locating pins 186 can be used to quickly and easily align the tower 112 with the base 110. Additionally, a clamp stopper 192 can be used to prevent the clamping mechanism 178 from traveling too far and coming into contact with the cutter 114.

According to the disclosed embodiment of the invention, the tower 112 includes three sensor devices 190(e-g). Sensor device 190e detects when the clamping mechanism 178 is in the "up" (or home) position. Sensor device 190f detects when the clamping mechanism 178 is in the vicinity of the clamp stopper 192. Accordingly, sensor device 190f and the clamp stopper 192 both function to prevent accidental contact with the cutter 114. Sensor device 190g detects the presence of the door 184. If an error signal is obtained from sensor device 190g, then operation of the substrate cutting device 100 is immediately halted.

Figure 17:
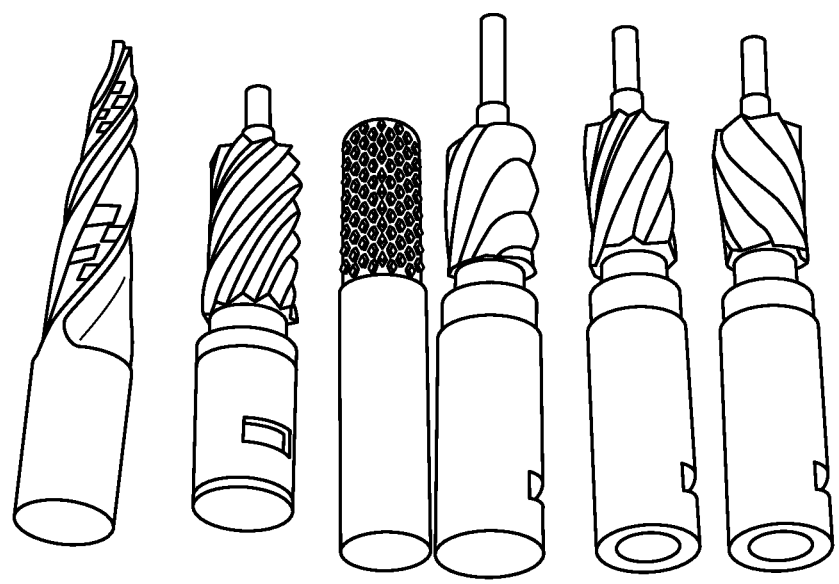
FIG. 17 illustrates alternative cutters that can be used in different embodiments of the present invention.
Figure 18:
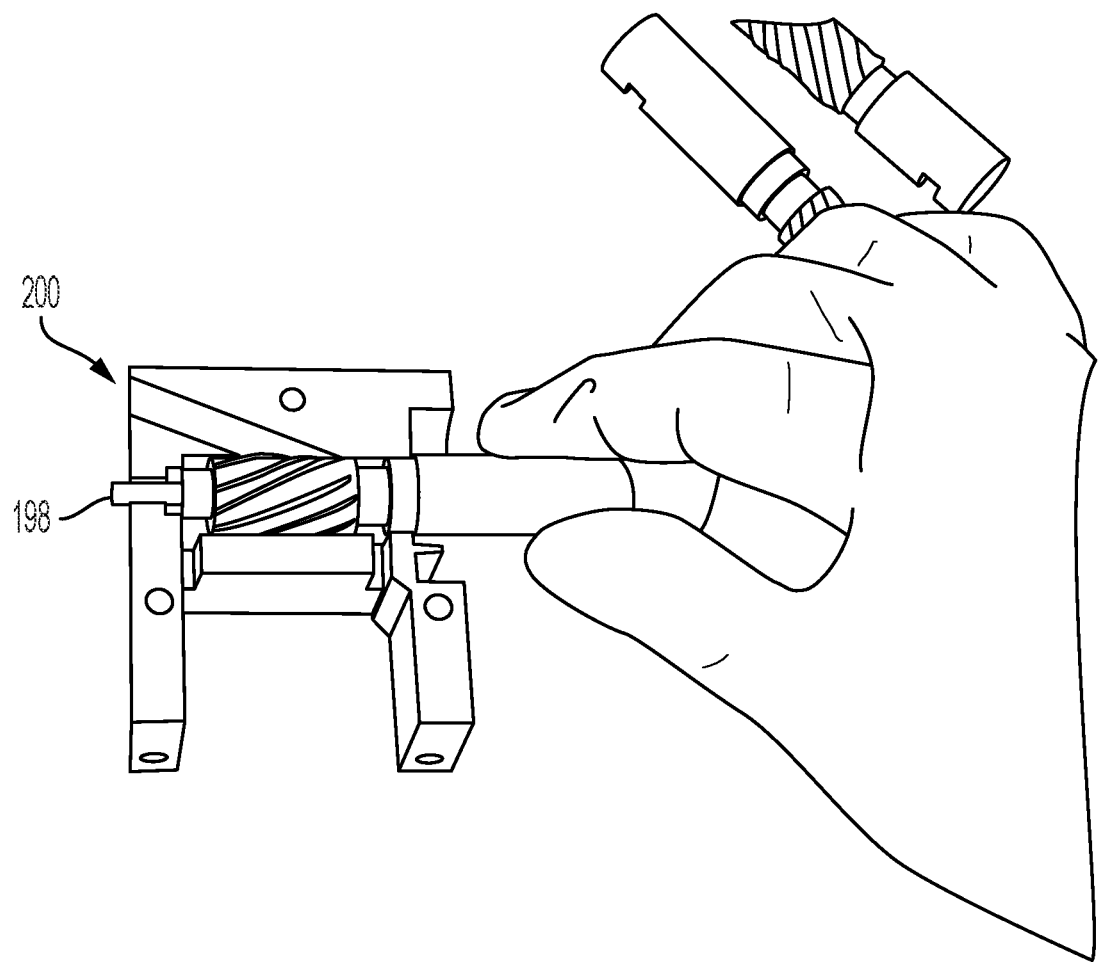
FIG. 18 illustrates an exemplary configuration for use with one of the alternative cutters shown in FIG. 17.

FIGS. 17 and 18 illustrates a plurality of wheel type cutters 198 (or wheel cutters) that can be used with an alternative embodiment of the present invention. The wheel cutters 198 are mounted on a base such that they may be rotated and brought into contact with the substrate. The wheel cutters 198 can be designed with various features to produce fibers having desired properties. For example, the thread depth of the wheel cutters 198 can be increased in order to produce fibers having an increased thickness. Varying the pitch of the wheel cutter 198 will effect the length and curvature of the fibers produced. As shown in FIG. 19, a substrate path 200 is used to bring the substrate in contact with the wheel cutter 198. When the pitch of the wheel cutter 198 rotates clockwise relative to the substrate, a "pulling" effect results. This requires less force on the substrate during the cutting process, and produces fibers that are short and curly. When the pitch of the wheel cutter 198 rotates counter-clockwise relative to the substrate, a greater force must be applied in order to maintain contact with the wheel cutter 198. However, the resulting fibers can be longer and will have very consistent dimensions.

FIG. 19 is a flowchart illustrating the steps performed to produce fibers in accordance with an exemplary embodiment of the present invention. The process begins at step S300. At step S310, the substrate is loaded into the substrate chute. At step S312, all of the access doors (i.e., cutter access door, receptacle door, and tower door) are closed. At step S314, the sensor devices are checked to verify that all access doors are currently closed. If any of the access doors are open, control passes to step S316. The system waits a predetermined amount of time, for example 10 seconds, and checks the sensor devices again. Alternatively, the system could continuously check the sensor devices until all access doors are closed.

Once all access doors are determined to be closed, control passes to step S318. The clamp is then activated. As previously discussed, this can be accomplished by second actuation unit applying pressure on the substrate. At step S320, the cutter is activated. At step S322, the sensor devices are checked to see if the substrate size has been reduced to a thickness, which is less than a minimum value. If the substrate thickness is greater than the minimum value, then control returns to step S322 and the cuter remains active, i.e., continues to cut the substrate. If the substrate thickness is less than or equal to the minimum value, then the system is stopped as step S326.

As illustrated by the dashed lines, the system continuously monitors the state of the sensor devices throughout the process. Thus, if any of the access doors are opened during operation of the substrate cutting device, control will pass to step S316 and the system will be immediately halted. As previously discussed, this is done, in part, to prevent injury to an operator. The system continues to operate until the either the substrate thickness reaches the minimum size, or one of the access doors is opened.

Example 1

Diaphysyl shafts (total of approximate 520 grams wet weight of bone material) from the long bones and ribs of a given donor (human donor information is confidential) were mechanically debrided (as disclosed in co-pending U.S. patent application Ser. No. 10/108,104, incorporated by reference herein) to remove associated periosteal tissue and bone marrow in the intramedulary canal. The shafts and ribs were then cut into linear pieces with widths, thickness, and lengths approximating <45 mm x<45 mm x<6 cm using a bone saw. A cut piece of cortical bone (wet weight 48 grams) was then loaded individually into the load chute of the cutting device and the clamping cylinder was locked into the closed position. The cutting slide having the cutting blade disposed therein was activated and cut fiber bone was collected into the receiving bin. A total of 42 grams of fiber bone were accumulated during the 60 cutting cycles (cutting cycle equals one back/forthpass of the cutter/cutter slide across the bone surface) for approximately 70 seconds with additional bone materials being added to the feeder chute at each cutting event. After each cutting event, another cortical shaft and/or cortical pieces were added and another cutting event was initiated. The amount of the bone materials loaded into the chute for each cutting event varied. However, the number of cutting events performed were sufficient to accumulate a bulk fiber mass of approximately 490 grams (wet weight).

The cut fiber bone was stored in a sterile container in the freezer (minus 80 C.) for three days. Prior to demineralization, the cut fiber bone was cleaned with LifeNet's patented ALLOWASH™ technology. For demineralization, a total of 463 grams of bone materials were added to the Pulsatile Acid Demineralization (PAD) chamber (as disclosed in co-pending U.S. patent application Ser. No. 09/655,371 herein incorporated by reference) and demineralized to 2.5% residual calcium using 2 cycles of 0.5 N HCl and acid volumes of 4.0 liters/cycle and 3.0 liters/cycle, 1 cycle of ultrapure water of 3.0 liters/cycle, and 2 cycles ultrapure water plus buffer of 3.0 liters/cycle to terminate the demineralization process. The bone fibers were finally washed in 3.0 liters of ultrapure water and stored frozen at minus 80 C in a sterile container.

Figure 3:
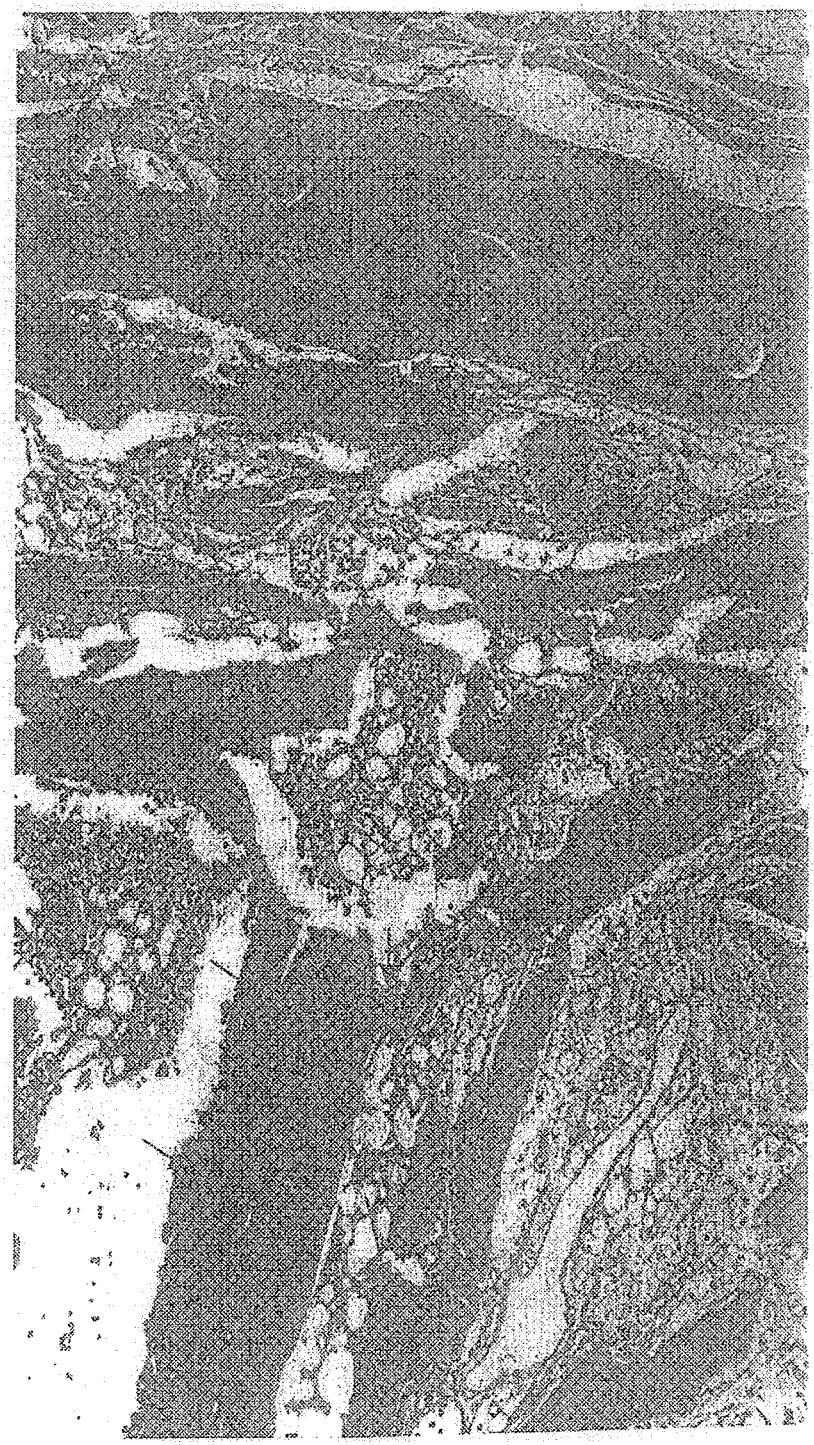
FIG. 3 depicts a histology slide stained with Hematoxylin and Eosin of bone fibers of the present invention when implanted intramuscularly in an athymic (nude) mouse bioassay. The arrows (.fwdarw.) indicate sites of new bone formation.
Figure 4:
FIG. 4 photographically illustrates the bone fibers when combined with cancellous particle bone to create a composite matrix as used to bind stem cells from blood, bone marrow, or similar cellular composition.

Aliquots of the demineralized fiber bone were removed from a sterile container and transferred to the animal implantation laboratory. Aliquots of fiber bone (20 and 40 mg wet weight) were manually compacted and implanted intramuscularly into the hindquarters of athymic (nude) mice as compressed fiber bone materials using established Institutional Animal Care and Use Committee approved protocols (Old Dominion University). After 28 days of implantation, the implanted materials were explanted and the explants fixed in formaldehyde. The fixed explants were embedded in paraffin and sectioned for use in preparation of histology slides. The prepared histology slides were stained using Hematoxylin and Eosin (H&E staining) and viewed under the microscope for induced new bone formation. The induced new bone formation is illustrated in FIG. 3. Induced new bone formation was determined using histomorphometry and the bone materials were determined to have induced significantly more new bone than non-osteoinductive controls, i.e. the fiber bone was deemed to be osteoinductive using the nude mouse bioassay model.

Example 2

In Vitro Attachment of Fibroblast Cells to Fiber Bone

The attachment of fibroblast cells to fiber bone may be quantitated using the methyltetrazolium dye assay method (MTT) where metabolic activity reduces the methyltetrazolium dye to an insoluble (chromogenic) substrate that can be quantitated using the spectrophotometer. In this particular assessment, cell attachment is compared with cell attachment to particle bone (cortical bone ground, using impact fragmentation) ground to a particle size range of 250 to 710 microns, demineralized and used in equal gram equivalents.

Fibroblast cells (NIH 3T3) were chosen for the study in that these cells represent relatively undifferentiated cells present in the body and are presumed to represent those cells that primarily migrate to the site of implantation of demineralized bone such as used in nude (athymic) mouse implant studies to assess the osteoinductivity of demineralized bone.

Fibroblast cells ($1-5 \times 10^5$ cells/ml) grown in RPMI 1640 tissue culture medium (supplemented with 10%, by volume, fetal calf serum (FCS) and glutamine) were harvested from the T-75 culture flasks using trypsinization. The residual trypsin associated with the cells put into suspension was neutralized by resuspending the cells in fresh RPMI 1640 tissue culture medium (supplemented with 10% FCS). Demineralized fiber bone (100 mg, wet weight) was aliquoted into replicate (20) 15 ml sterile centrifuge tubes and demineralized particle bone (100 mg, wet weight) was aliquoted into replicate (20) 15 ml sterile centrifuge tubes. The twenty tubes of fiber bone and 20 tubes of particle bone were divided into two groups each of 10 replicates such that one group of 10 would be incubated with tissue culture medium without cells and the remaining group of 10 would be incubated with tissue culture medium with cells. Each tube received 5 mls of medium (medium containing or not containing cells) such that tubes receiving medium with cells received approximately $5 \times 10^5$ to $1 \times 10^6$ cells/100 mg of demineralized bone (fiber or particle). The tubes were statically incubated at 37 C for one (1) hour, at which time the medium was decanted off of the bone and fresh medium (5 ml) added and decanted to affect a "washing" of the demineralized bone. This "washing" process was repeated a total of three times. All steps were conducted using aseptic techniques such that the demineralized bone could be incubated overnight at 37 C to permit the attached cells to proliferate.

Following the overnight incubation, the demineralized bone/medium/"cells" (if added in the centrifuge tube) were vigorously vortexed to dislodge cells and the medium decanted to a fresh centrifuge tube. The dislodged cells were concentrated by low speed (1,500 to 2,000 rpm in a clinical table top centrifuge) centrifugation and the medium decanted. The cell pellets were assayed using the standard MTT assay and the numbers of cells "quantitated" by comparison to a standard curve where known numbers of cells were aliquoted into centrifuge tubes, centrifuged to concentration and assayed.

Background absorbance values were obtained using the demineralized bone (fiber and particle) incubated in the absence of cells. On average, the fiber bone presented $1-5 \times 10^3$ cells/100 mg of bone whereas the particle bone presented approximately $2-4 \times 10^2$ cells/100 mg of bone, i.e., an approximate 10-fold greater numbers of cells per unit wet weight of fiber bone to particle bone.

Example 3

In Vivo Attachment of Cells to Fiber Bone

Implantation of biomaterials into muscle pouches of athymic (nude) mice (two implants/mouse, implanted bilaterally in the gluteal region of the mouse) represents the current "gold-standard" method of assessing the osteoinductivity of such biomaterials. Between 10 and 20 mg (dry weight) of biomaterials (demineralized bone in this example) are rehydrated with isotonic saline and implanted just under the fascia using a dental amalgam tool (such as typically used by a dentist to add the filing materials to a cavity formed in teeth).

Figure 20A:
FIGS. 20A and 20B are histology slides stained with H&E of human bone fibers of the present invention (FIG. 20A) and human particle bone used as a control (FIG. 20B) implanted intramuscularly in an athymic (nude) mouse bioassay as set forth in Example 3 and, after 28 days, explanted and fixed in buffered formalin. The arrows (.fwdarw.) indicate sites of new bone formation.
Figure 20B:

In this study, human "shaved" (fiber) bone and human "DMB Positive Control" (particle) bone were implanted into muscle pouches of athymic mice (two implants/mouse and three mice per implant group). The implanted materials were explanted after 28 days, and the explants (explanted as "hard" nodules) were fixed in buffered formalin. The samples were decalcified and embedded in paraffin prior to preparation of histological sections for staining (hematoxalin/eosin; H&E). As illustrated in FIGS. 20A (bone fibers) and 20B (control), both demineralized bone materials were osteoinductive, in that new bone formation was clearly visible in the histology sections. However, cells are more clearly visible along the edges of the fiber bone materials as shown in FIG. 20A as compared to the comparable edges of the particle bone materials as shown in FIG. 20B suggesting that cells migrating to the implant sites were more likely to bind tightly to the fiber bone than to the particle bone (although both demineralized bone biomaterials induced cells infiltrating the implant materials to differentiate into "osteoblast" or "osteoblast-like" cells and synthesize new bone matrix that stained comparably to implant bone).

While the invention has been described in connection with specific embodiments thereof, it will be understood that it is capable of further modifications and this application is intended to cover any variations, uses, or adaptations of the invention following, in general the principles of the invention and including such departures from the present disclosure as within known or customary practice within the art to which the invention pertains and as may be applied to the essential features hereinbefore set forth as follows in the scope of the appended claims. Any references including patents and published patent applications cited herein are incorporated herein in their entirety.

The invention claimed is:

1. A frozen allogeneic bone material composition stored in a sterile container for implantation in a human patient, comprising:
   (a) human demineralized cortical bone,
   (b) human non-demineralized bone comprising cortical bone, cancellous bone, or a combination thereof,
   (c) osteocytes, and
   (d) a biological fluid, wherein the biological fluid is a biological fluid selected from the group consisting of plasma, bone marrow, blood, a blood product and a combination thereof,
   wherein the allogeneic bone material composition is frozen and stored in the sterile container.

2. The allogeneic bone material composition of claim 1, wherein the composition further comprises pre-osteoblasts.

3. The allogeneic bone material composition of claim 1, wherein the composition further comprises osteoblasts.

4. The allogeneic bone material composition of claim 1, wherein the composition further comprises cells selected from the group consisting of stem cells, connective tissue progenitor cells, and combinations thereof.

5. The allogeneic bone material composition of claim 1, wherein the composition further comprises stem cells.

6. The allogeneic bone material composition of claim 1, wherein the osteocytes are suitable for forming an osteoid.

7. The allogeneic bone material composition of claim 1, wherein the demineralized cortical bone is in the form of particles.

8. The allogeneic bone material composition of claim 1, wherein the demineralized cortical bone is in the form of fibers.

9. The allogeneic bone material composition of claim 8, wherein the bone fibers have a length and thickness, and wherein the fiber length is greater than 10 to 200 times the fiber thickness.

10. The allogeneic bone material composition of claim 8, wherein the bone fibers have a length and thickness, and wherein the fiber length is greater than 40 to 100 times the fiber thickness.

11. The allogeneic bone material composition of claim 8, wherein the bone fibers have a length, and wherein the average fiber length is from 1 mm to 100 mm.

12. The allogeneic bone material composition of claim 8, wherein the bone fibers have a length, and wherein the average fiber length is from 20 mm to 30 mm.

13. The allogeneic bone material composition of claim 1, wherein the demineralized cortical bone contains calcium at a level of from 0.1 wt % to 7.7 wt %.

14. The allogeneic bone material composition of claim 1, wherein the demineralized cortical bone contains calcium at a level of from 1 wt % to 4 wt %.

15. The allogeneic bone material composition of claim 1, wherein the non-demineralized bone comprises cortical bone.

16. The allogeneic bone material composition of claim 1, the non-demineralized bone comprises cancellous bone.

17. The allogeneic bone material composition of claim 1, the non-demineralized bone is in the form of chunks.

18. The allogeneic bone material composition of claim 1, the non-demineralized bone is in the form of particles.

19. The allogeneic bone material composition of claim 1, further comprising a bone growth agent.

20. The allogeneic bone material composition of claim 19, wherein the bone growth agent is selected from the group consisting of bone morphogenic proteins, angiogenic factors, growth and differentiation factors, mitogenic factors, osteogenic factors, chondrogenic factors and combinations thereof.

* * * * *